United States Patent [19]

Hayano

[11] Patent Number: 5,719,405
[45] Date of Patent: Feb. 17, 1998

[54] PARTICLE INSPECTING APPARATUS AND METHOD USING FOURIER TRANSFORM

[75] Inventor: Fuminori Hayano, Tokyo, Japan

[73] Assignee: Nikon Corporation, Tokyo, Japan

[21] Appl. No.: 595,347

[22] Filed: Feb. 1, 1996

Related U.S. Application Data

[63] Continuation of Ser. No. 306,896, Sep. 16, 1994, abandoned, which is a continuation-in-part of Ser. No. 112,383, Aug. 27, 1993, abandoned.

[30] Foreign Application Priority Data

| Sep. 1, 1992 | [JP] | Japan | 4-233819 |
| Sep. 3, 1992 | [JP] | Japan | 4-235056 |
| Sep. 3, 1992 | [JP] | Japan | 4-235057 |
| Sep. 3, 1992 | [JP] | Japan | 4-235058 |
| Sep. 17, 1993 | [JP] | Japan | 5-231278 |
| Sep. 17, 1993 | [JP] | Japan | 5-231279 |

[51] Int. Cl.⁶ ............................................ G01N 21/88
[52] U.S. Cl. ...................... 250/559.41; 250/559.45; 356/71; 356/237
[58] Field of Search ........................ 250/571, 572, 250/562, 563, 559.41, 559.45, 559.46, 559.47, 559.48; 356/237, 71; 382/31

[56] References Cited

U.S. PATENT DOCUMENTS

| 3,305,834 | 2/1967 | Cooper et al. | 340/146.3 |
| 3,614,232 | 10/1971 | Mathisen | 356/71 |
| 3,771,124 | 11/1973 | McMahon | 340/146.3 E |
| 4,330,775 | 5/1982 | Iwamoto et al. | 340/146.3 P |
| 4,806,774 | 2/1989 | Lin et al. | 250/550 |
| 4,889,998 | 12/1989 | Hayano et al. | 250/563 |
| 5,172,000 | 12/1992 | Scheff et al. | 250/550 |
| 5,264,912 | 11/1993 | Vaught et al. | 356/237 |

Primary Examiner—Stephone B. Allen
Attorney, Agent, or Firm—Shapiro and Shapiro

[57] ABSTRACT

A particle inspecting apparatus capable of detecting only particles without depending on conditions such as a density, a configuration, etc. of an original pattern of an object to be inspected is provided. The apparatus includes a light irradiating device for irradiating the inspected object with a beam of light and a condensing optical system for condensing the beam from the inspected object. The apparatus also includes a light limiting device, disposed in the vicinity of a Fourier transform plane for the inspected object in the condensing optical system, for admitting a passage of the beam corresponding to only a part of a Fourier transform pattern of the beam from the inspected object, a relative position shiftable device for shifting relative positions of the Fourier transform pattern of the beam from the inspected object and the light limiting device and a detecting device for detecting the particle on the basis of the beam passing through the light limiting device.

9 Claims, 19 Drawing Sheets

PARTICLE INSPECTING APPARATUS AND METHOD USING FOURIER TRANSFORM

This is a continuation of application Ser. No. 08/306,896 filed Sep. 16, 1994, which is a continuation-in-part of application Ser. No. 08/112,383 filed Aug. 27, 1993, both now abandoned.

BACKGROUND OF THE INVENTION

1. Field of the Invention

The present invention relates generally to an apparatus for inspecting particles and, more particularity, to the particle inspecting apparatus suitable for an application to inspecting dusts or particles on the inspected object, having a regular or periodic structure, such as a mask for exposure, a reticle or a wafer after the exposure or a glass substrate like an optical disk and an iron plate or a mesh that are employed especially when manufacturing, e.g., a semiconductor element by use of the photolithography.

2. Related Background Art

The particle inspecting apparatus has hitherto been used for inspecting the dusts and the particles on the inspected object, having the regular (periodic) structure, such as the mask for exposure, the reticle or the wafer after the exposure or the glass substrate like the optical disk and the iron plate or the mesh that are employed when manufacturing, e.g., the semiconductor element by use of the photolithography. The photomask or the reticle is hereafter generally called a reticle.

FIG. 18 illustrates a conventional particle inspecting apparatus.

Referring to FIG. 18, a beam of light L1 emitted from a light source 1 is deflected by an oscillation mirror (a galvano-scanner mirror or a polygon scanner mirror) 2 and is incident on a scan lens 3. With oscillations (rotations) of the oscillation mirror 2, scanning along scan lines 5 on an inspected surface 4 is performed by using a beam of light L2 outgoing from the scan lens 3.

Then, the beam L2 scans the scan lines 5 through the oscillation mirror 2. At the same time, the inspected surface 4 is moved at a speed lower than a scanning period of the beam L2 in an R-direction perpendicular to the scan line 5 by an unillustrated moving means. The scanning by the beam L2 is conducted in such directions (the direction along the scan line 5 and the R-direction), whereby the entire inspected surface 4 can be scanned by the beam L2.

In the case of inspecting a dust, the beam L2 falls on an area where a particle 6 like the dust exists on the inspected surface 4. Hereupon, beams of scattered light are generated therefrom. Further, the beam L2 falls on an area where a periodic structure (hereinafter generally termed a [pattern]) 7 exists, the structure 7 being different from the particle like the dust on the inspected surface 4 and exemplified in the form of, e.g., circuit patterns on the reticle and on the wafer or grooves of the optical disk. Then, beams of diffracted light L4 are generated from the pattern 7.

The object to be detected by the particle inspecting apparatus is not, however, the pattern 7 originally existing on the inspected surface 4 but the particle 6 which should not originally exist. Hence, only the particle, which is to be distinguished from the pattern 7, has to be detected. For this purpose, photodetectors 8A, 8B, 8C are disposed in face-to-face relationship with the scan line 5 in the directions different from each other in FIG. 19A.

The beams of scattered light L3 generated from the particle 6 such as the dust are defined as beams of isotropic scattered light generated substantially in every direction. Contrastingly, the diffracted light L4 generated from the pattern 7 is defined as light (exhibiting a high directivity) emitted in spatially discrete directions.

The particles are distinguished from the circuit pattern by making most of a difference between the properties described above.

If the light is detected by all the photodetectors 8A, 8B, 8C, these beams are judged to be the scattered light from the particle. If there exists even one photodetector among the photodetectors 8A, 8B, 8C, the light is judged to be the diffracted light from the pattern. It is thus possible to detect only the particle 6 in distinction from the pattern 7.

The conventional particle inspecting apparatus stated above, however, presents the following drawback. Depending on the density or the configuration of the pattern on the inspected surface 4, even the diffracted light from the pattern is incident on all the photodetectors 8A, 8B, 8C, resulting in a misjudgment of being the particle.

Now, supposing that there is a particle inspecting method capable of exactly discriminating the pattern-light from the particle-light, it is undesirable that the time spent for the inspection increases so much. Particularly, if the inspected surface 4 has a large area to be inspected, it is desirable that the inspection time be as short as possible.

Further, an often-adopted practice in recent years is that a pellicle (dust adhesion preventive film) 10 is, as illustrated in FIG. 19B, coated over a reticle 4 while being surrounded with a pellicle frame serving as a support frame so as not to adhere the dust directly to a pattern forming surface (or double surfaces) of the reticle 4. The pellicle 10 is a light transmitting thin film having a thickness on the order of 1 μm. The pellicle frame 9 is a metal frame composed of aluminum, etc. FIG. 19A is a view depicting a dust inspecting apparatus for effecting an inspection on the reticle 4 over which the pellicle 10 is coated. The same members as those in FIG. 18 are marked with the like numerals. The apparatuses of FIGS. 19A and 18 are constructed the same.

As illustrated in FIG. 19A, however, when inspecting the particles on the surface of the reticle 4 with the pellicle 10 coated thereon, the beam L2 undergoes vignetting by the pellicle frame 9, or optical axes AX1–AX3 of the beams traveling toward the photodetectors 8A–8C are also subjected to vignetting by the pellicle frame 9. This consequently conduces to such a drawback that it is difficult to perform the inspection on the inspected surface of the reticle 4 in close proximity to the pellicle frame 9.

SUMMARY OF THE INVENTION

It is a primary object of the present invention to provide a particle inspecting apparatus capable of detecting only particles without depending on a density and a configuration of an original pattern of an object to be inspected.

To accomplish this object, according to one aspect of the present invention, there is provided an apparatus for inspecting particles on an object to be inspected, comprising: a light irradiating means for irradiating the inspected object with a beam of light; a condensing optical system for condensing the beam from the inspected object; a light limiting means, disposed in the vicinity of a Fourier transform plane for the inspected object in the condensing optical system, for admitting a passage of the beam corresponding to only a part of a Fourier transform pattern of the beam from the inspected object; a relative position shiftable means for shifting relative positions of the Fourier transform pattern of the beam from the inspected object and the light limiting means; and a detecting means for detecting the particles on the basis of the beam passing through the light limiting means.

The optical principle as a basis of the present invention will be explained with reference to FIG. 1.

Turning to FIG. 1, an inspected surface 11 is irradiated with a beam of light L. For simplifying the explanation herein, however, it is assumed that the inspected surface 11 is a object which partially transmits the light, and the beam L falls perpendicularly from the rear side of the inspected surface 11. The present invention is, however, similarly applicable to the fall-illumination as well as to the transmitting illumination. Further, the present invention is established by any illumination method, whether in a bright field or in a dark field.

A light receiving lens 12 is disposed in an outgoing direction of the beam L from the inspected surface 11. A Fourier transform image 13F of a pattern 13 on the inspected surface 11 is formed on an image-side pupil plane P1 of the light receiving lens 12. The pupil plane P1 of the light receiving lens 12 is also referred to as a Fourier transform plane. Further, a lens 14 is disposed in an outgoing direction of the beam from the pupil plane P1. The Fourier transform image 13F is formed in reduction on a second pupil plane P2 conjugate to the pupil plane P1 through the lens 14. A light receiving surface of a photodetector 15 is disposed on the second pupil plane P2. The reduced image on the second pupil plane P2 is photoelectrically converted by the photodetector 15. Accordingly, a position 11C is conjugate to the inspected surface 11 through the light receiving lens 12 and the lens 14 is different from the second pupil plane Paying attention to FIG. 1, any optical element is disposed in a position on the pupil plane P1, but the pupil plane P1 is an imaginary plane. More specifically, according to a geometry of FIG. 1, all the optical information on the inspected surface 11 is incident on the photodetector 15. For this reason, if left as it is, and when the particles exist, the optical information of the particles is incident on the photodetector 15 together with the optical information of the original pattern 13 on the inspected surface 11. It is therefore difficult to detect only the particle in distinction from the pattern.

Under such circumstances, the present invention provides a construction as shown in FIG. 2. Referring to FIG. 2 wherein the same elements as those in FIG. 1 are marked with the like numerals, an optical positional relationship between the inspected surface 11, the light receiving lens 12, the pupil plane P1, the lens 14, the second pupil plane P2 and the photodetector 15 is the same as that in FIG. 1. Referring again to FIG. 2, a light intercepting plate 17 formed with an aperture 16 is further provided within the pupil plane P1. Varied at this time are relative positions of the Fourier transform image 13F (see FIG. 1) of the pattern 13 that is formed on the pupil plane P1 and of the aperture 16. Then, it may happen that a beam spot in the Fourier transform image 13F does not exit in the aperture 16, or alternatively, the beam spot is, though it exists in the aperture 16, feeble in quantity. In contrast with this, the scattered light produced from the particle such as a dust existing on the inspected surface 11 is, as already mentioned, produced with isotropy. Therefore, even when shifting the relative positions of the Fourier transform image 13F and the aperture 16 in that manner, the quantity of the scattered light passing through the aperture 16 increases and decreases sluggishly or exhibits almost no change. Only the particle is detected in distinction from the pattern by exploiting this characteristic.

At this time, the light passing through the aperture 16 is detected by the photodetector 15 located in the pupil conjugate position. The relative positions of the Fourier transform image 13F and the aperture 16 are determined to minimize a photoelectric conversion signal S of the photodetector 15. It then follows that the spot of the Fourier transform image 13F does not pass through the aperture 16 at that time, and, if it passes therethrough, the light quantity thereof is small. The result is that comparatively a larger amount of optical information from the particles than from the Fourier transform image 13F passes through the aperture 16. At this time, an image of the inspected surface 11 is viewed with the aid of the light passing through the aperture 16, whereby only the particle can be detected. A viewing means may involve the use of an imaging means such as a charge coupled type imaging device (CCD), or the image may be visually viewed. The above-mentioned is the principle of the present invention.

A first means is a driving means for shifting the position of the aperture 16 by moving the light intercepting plate 17 within the pupil plane P1. A second means is an incident direction variable means for varying an incident vector of the beam L, i.e., an incident direction and an incident angle upon the inspected surface 11, with the position of the aperture 16 being fixed. The former (first) means will be explained with reference to FIGS. 3A and 3B, while the latter (second) means will be explained referring to FIG. 4.

FIG. 3A illustrates the pupil plane P1 of FIGS. 1 and 2 as viewed in the direction perpendicular to this pupil plane P1. Paying attention to FIG. 3A, the symbol represents a Fourier transform image of the pattern 13 of FIG. 1. The aperture 16 is a part of the light intercepting plate 17 of FIG. 2. Let <C> be the positional vector indicating a position of the aperture 16 on the basis of an origin P0 (a previously given origin P0) on the pupil plane P1. The photoelectric conversion signal S of the photodetector 15 of FIG. 2 changes as shown in FIG. 3B with respect to a variation in the positional vector <C>. To be more specific, when the beam spot of the Fourier transform image 13F passes through the aperture 16, the photoelectric conversion signal S increases. If not, however, the aperture 16 transmits the particle information other than the pattern 13, and, therefore, the photoelectric conversion signal S is small. For this reason, only the particle is detectable by detecting a minimum value $S_{min}$ of the photoelectric conversion signal S of FIG. 13B. Concretely, there are predetermined a couple of threshold values $S_{TH1}$ and $S_{TH2}$ ($S_{TH2}>S_{TH1}>0$) with respect to a predetermined particle. When the minimum value $S_{min}$ of the photoelectric conversion signal S satisfies the following formula, it is judged that the particle exists.

$$S_{TH1} \leq S_{TH2}$$

On this occasion, the minimum value $S_{min}$ undergoes almost no influence of the original pattern 13 of the inspected surface 11. Hence, only the particle can be accurately detected without depending on the pattern 13.

Given next is an explanation of a case where the incident vector of the beam L varies in conjunction with FIG. 4.

Turning to FIG. 4, a spot 18 of 0th-order diffracted light of the pattern 13 is formed on the pupil plane P1, wherein $<e_0>$ is the initial incident vector (unit-length vector parallel to the beam n which is incident on the inspected surface 11) of the beam L. Let $<C_0>$ be the positional vector of the spot 18 with respect to the aperture 16 fixed onto the pupil plane P1.

Then, when changing the incident direction and the incident angle of the incident beam L upon the inspected surface 11, the incident vector becomes $<e'>$. At this time, the spot of the 0th-order diffracted light on the pupil plane P1 turns out to be a spot 18'. The positional vector of the spot 18' with respect to the aperture 16 becomes a vector <C'>. However, <C$_0$>≠<C'>. Namely, as shown in FIG. 3, the positional vector <C$_0$> varies absolutely in the same way as shifting the position of the aperture 16. It is therefore possible to obtain only the optical information of the particle even by changing the incident vector, i.e., the incident direction.

Further, in FIG. 2, when rotating the inspected surface 11, the Fourier transform pattern 13F of the pattern 13 of the inspected surface 11 rotates on the pupil plane P1. Accordingly, it follows that the positional vector <C> of FIGS. 3A and 3B is shifted also by rotating the inspected surface 11. Only the optical information of the particle can be thereby obtained.

Moreover, for enhancing a capability of detecting the particle, the above-mentioned three methods may be combined, or a plurality of apertures 16 may also be formed with the pupil space. The present invention, as a matter of course, includes the following arrangements. For instance, a single piece of light receiving lens 12 is prepared, and the plurality of apertures 16 may be formed within the pupil plane P1 of the light receiving lens 12. Not a single but a plurality of light receiving lenses 12 are prepared, and there are provided a plurality of pupil planes and a plurality of apertures.

According to the present invention, the light receiving means is capable of receiving only the beam relative to the particle among beams of light from the inspected object through the relative position shiftable means. There is such an advantage that only the particle can be detected without depending on the density and the configuration of the original pattern on the inspected object.

Besides, if the relative position shiftable means is a driving means for shifting a position of the aperture means in the vicinity of the Fourier transform plane of the condensing optical system, the configuration may he simple. Further, the relative position shiftable means is an incident direction variable means for varying the incident direction, upon the inspected object, of the inspection beam with which the light irradiating means irradiates the inspected object, this arrangement is effective depending on the inspected object. In addition, if the relative position shiftable means is a rotating means for rotating the inspected object, the configuration is also simple.

According to another aspect of the present invention, there is provided an apparatus for inspecting particles on an object to be inspected, comprising: a light irradiating means for irradiating the inspected object with a beam of light; a condensing optical system for condensing the beam from the inspected object; a light limiting means, disposed in the vicinity of a Fourier transform plane for the inspected object in the condensing optical system, for admitting a passage of the beam corresponding to only a part of a Fourier transform pattern of the beam from the inspected object; a light receiving means for receiving the beam passing through the light limiting means and outputting a photoelectric signal corresponding to the beam received; a relative position shiftable means for shifting relative positions of the Fourier transform pattern of the beam from the inspected object and the light limiting means to minimize the photoelectric signal; a transform optical system for forming a conjugate image of the inspected object by performing an inverse Fourier transform of the beam passing through the light limiting means; and a viewing means for viewing the conjugate image.

According to the present invention, the following advantages are given. Only the beam relative to the particle among the beams from the inspected object can be transferred by the relative position shiftable means via the light limiting means to the viewing means. Only the particle can be detected without depending on the density and the configuration of the original pattern on the inspected object. Besides, the configurations, etc. of the particle can be viewed by the viewing means. Further, when the light receiving means is disposed in the vicinity of the locating plane of the light limiting means or another light limiting means equivalent thereto, the construction is simple.

Moreover, there is disposed the deflection optical system for deflecting a part of beams passing through the light limiting means. When the light receiving means receives the beam deflected by this deflection optical system, the particle can be detected at a higher speed.

It is another object of the present invention to provide a particle inspecting apparatus and method each capable of detecting only the particle without depending on the density and the configuration of the original pattern on the inspected object as well as reducing a inspection time.

According to still another aspect of the present invention, there is provided an apparatus for inspecting particles on an inspected object, comprising: a light irradiating means for irradiating the inspected object with a beam of light; a condensing optical system for condensing the beam from the inspected object; a moving means for shifting relative positions of the inspected object and the light irradiating means; a light limiting means, disposed in the vicinity of a Fourier transform plane for the inspected object in the condensing optical system, for admitting a passage of the beam corresponding to only a part of a Fourier transform pattern of the beam from the inspected object; a light receiving means for receiving the beam passing through the light limiting means and outputting a photoelectric signal corresponding to the beam received; a relative position shiftable means for shifting relative positions of the Fourier transform pattern of the beam from the inspected object and the light limiting means; a judging means for judging the particles on the basis of a signal from the light receiving means; and a control means for controlling the relative position shiftable means to minimize the photoelectric signal of the light receiving means through the relative position shiftable means on the basis of pattern information on the inspected object.

According to a further aspect of the present invention, there is provided an apparatus for inspecting particles on an inspected object, comprising: a light irradiating means for irradiating the inspected object with a beam of light; a condensing optical system for condensing the beam from the inspected object; a moving means for shifting relative positions of the inspected object and the light irradiating means; a light limiting means, disposed in the vicinity of a Fourier transform plane for the inspected object in the condensing optical system, for admitting a passage of the beam corresponding to only a part of a Fourier transform pattern of the beam from the inspected object; a transform optical system for effecting an inverse Fourier transform of the beam passing through the light limiting means to form a conjugate image of the inspected object; a viewing means for viewing the conjugate image; a light receiving means for receiving the beam passing through the light limiting means and outputting a photoelectric signal corresponding to the beam received; a relative position shiftable means for shifting relative positions of the Fourier transform pattern of the beam from the inspected object and the light limiting means; a control means for controlling the relative position shiftable means to minimize the photoelectric signal from the light receiving means when the light irradiating means irradiates a first inspection area of the inspected object with the beam through the moving means; a memory means for storing the photoelectric signal of the light receiving means; and a comparing means for comparing the photoelectric signal of the light receiving means with the photoelectric signal stored when the light irradiating means irradiates a second inspection area of the inspected object with the beam through the moving means and for controlling the relative position shiftable means to minimize the photoelectric signal of the light receiving means when the photoelectric signal of the light receiving means and the photoelectric signal stored are different from each other in excess of a predetermined allowable range.

According to still further aspect of the present invention, there is provided a method of inspecting particles on an object to be inspected in a particle inspecting apparatus including: a light irradiating means for irradiating the inspected object with a beam of light for inspection; a condensing optical system for condensing the beam from the inspected object; a moving means for shifting relative positions of the inspected object and the light irradiating means; a light limiting means, disposed in the vicinity of a Fourier transform plane for the inspected object in the condensing optical system, for admitting a passage of the beam corresponding to only a part of a Fourier transform pattern of the beam from the inspected object; a light receiving means for receiving the beam passing through the light limiting means and outputting a photoelectric signal corresponding to the beam received; a relative position shiftable means for shifting relative positions of the Fourier transform pattern of the beam from the inspected object and the light limiting means; a transform optical system for forming a conjugate image of the inspected object by effecting an inverse Fourier transform of the beam passing through the light limiting means; and a viewing means for viewing the conjugate image, the method comprising the steps of: irradiating a first inspection area of the inspected object with the beam of the light irradiating means through the moving means and setting relative positions of the Fourier transform pattern of the beam from the inspected object and of the light limiting means to minimize the photoelectric signal of the light receiving means through the relative position shiftable means; storing the photoelectric signal of the light receiving means when in the set relative positions; viewing the conjugate image of the inspected object through the viewing means; and comparing the photoelectric signal of the light receiving means with the photoelectric signal stored when irradiating a second inspection area of the inspected object with the beam of the light irradiating means through the moving means. The step of comparing the photoelectric signal of the light receiving means with the photoelectric signal stored involves viewing the conjugate image of the inspected object as it is through the viewing means when the photoelectric signal of the light receiving means and the photoelectric signal stored are equal to each other within a predetermined allowable range but involves, when the photoelectric signal of the light receiving means and the photoelectric signal stored are different from each other in excess of the predetermined allowable range, viewing the conjugate image of the inspected object through the viewing means after setting relative positions of the Fourier transform pattern of the beam from the inspected object and the light limiting means to minimize the photoelectric signal of the light receiving means through the relative position shiftable means.

Now, an illumination area irradiated with the beam L on the inspected surface 11 is tentatively called a [field]. The information obtained in a position 11C conjugate to the inspected surface 11 is restricted to in-field information. When inspecting all the areas on the inspected surface 11, there may be used such methods as scanning the inspected object 11 with the beam L and moving the inspected object 11 through a stage or the like. The positional relationship between the aperture 16 and the Fourier transform image 13F is set to minimize the photoelectric conversion signal S of the photodetector 15 every time the field changes with the relative movements of the beam L and the inspected object 11. With repetitions of such an operation (hereinafter termed an [optimization of the aperture]), however, the inspection time increases.

Then, the optimization of the aperture is conducted in a first field (first illumination area) on the inspected surface 11. Thereafter, when moving to a second field (second illumination area), and if a quantity of light passing through the aperture 16 does not changes far from the light quantity in the case of the first field, no optimization of the aperture is effected. That is, the positional relationship between the aperture 16 and the Fourier transform image 13F in the second field remains the same as the positional relationship in the first field, and, in this state, the particle inspection is carried out. Contrastingly, if the quantity of light passing though the aperture 16 is remarkably different from the light quantity in the first field, the optimization of the aperture is performed.

In the great majority of cases, the optimizing conditions of the aperture are fixed even when the field changes especially in the mask or the reticle where the periodic pattern continues and the mesh or the grooves on the optical disk, etc. Hence, if the present invention is applied to such an arrangement that the inspected surface 11 has the above-stated periodic pattern which continues, the time of aperture optimization is considerably reduced in each field. The entire inspected surface 11 can be thereby inspected at the high speed.

According to the present invention, the following advantages are produced. Only the beam relative to the particle among the beams from the inspected object can be transferred by the relative position shiftable means via the light limiting means to the viewing means. Only the particle can be detected without depending on the density and the configuration of the original pattern on the inspected object. Besides, the configuration, etc. of the particle can be viewed by the viewing means. An additional advantage is that the relative position shiftable means is not necessarily operated in the second detecting area on the inspected object, and hence the inspection time decreases.

It is a further object of the present invention to provide a particle inspecting apparatus capable of detecting only the particle without depending on the density and the configuration of the original pattern on the inspected object and, at the same time, performing the particle inspection so that the beam is not intercepted by the pellicle frame even when the inspected object is fitted with the pellicle.

To accomplish this object, according to a yet further aspect of the present invention, there is provided a particle inspecting apparatus comprising: a light irradiating means for continuously irradiating the inspected object with beams of light from different directions; a moving means for shifting relative positions of the inspected object and the light irradiating means; a condensing optical system for condensing the beam from the inspected object; a light limiting means, disposed in the vicinity of a Fourier transform plane for the inspected object in the condensing optical system, for admitting a passage of the beam corresponding to only a part of areas of a Fourier transform pattern of the beam from the inspected object; a selecting means for selecting an area of the Fourier transform pattern of the beam from the inspected object which is to pass through the light limiting means; a light receiving means for receiving the beam passing through the light limiting means and outputting a photoelectric signal corresponding to the beam received; a transform optical system for forming a conjugate image of the inspected object by effecting an inverse Fourier transform of the beam passing through the light limiting means; a viewing means for viewing the conjugate image; and a control means for indicating at least one of an irradiating direction and/or an irradiating angle in and/or at which the light irradiating means irradiates the inspected object with the beam in accordance with an illumination area of the inspected object and an area of the Fourier transform pattern of the beam from the inspected object which is to be selected by the selecting means.

On that occasion, though omitted in FIG. 2, if the pellicle frame is mounted along the periphery of the inspected surface 11, there are restricted the beams receivable by the light receiving lens 12, a movable range of the aperture 16 and a variable range of the incident vector of the beam L. For this reason, even though the photodetector 15 seeks such a case as to minimize the quantity of light passing through the aperture 16, as a matter of fact, it may happen that the incident beam L and the received beam merely undergo vignetting by means of the pellicle frame. In some cases, a normal pattern on the inspected surface 11 is misjudged to be a particle.

Under such circumstances, the principle of the present invention is that the effective range of the incident vector of the beam L and the effective range of the position of the aperture 16 are initially set in accordance with the placement of the pellicle frame and the fields (illumination areas) on the inspected surface 11.

According to the present invention, the following advantages are provided. Regulated is a direction in which the light irradiating means irradiates the inspected object with the light for inspection. Only the beam relative to the particle among the beams from the inspected object can be transferred via the light limiting means to the viewing means. It is possible to detect only the particle without depending on the density and the configuration of the original pattern on the inspected object. Besides, the configuration, etc. of the particle can be viewed by the viewing means.

Additional advantages will be given as below. Even when the inspected object is mounted with the pellicle frame or the like, there are designated the inspection beam irradiating direction and angle from the irradiating means toward the inspected object or the area, selected by the selecting means, of the Fourier transform pattern of the beam from the inspected object in accordance with the illumination area of the inspected object. The particle inspection can be performed so that the light is not intercepted by the pellicle frame or the like.

BRIEF DESCRIPTION OF THE DRAWINGS

Other objects and advantages of the present invention will become apparent during the following discussion in conjunction with the accompanying drawings, in which.

DESCRIPTION OF THE PREFERRED EMBODIMENTS

A first embodiment of the present invention will hereinafter be described with reference to FIGS. 5A–7.

Figure 5A:
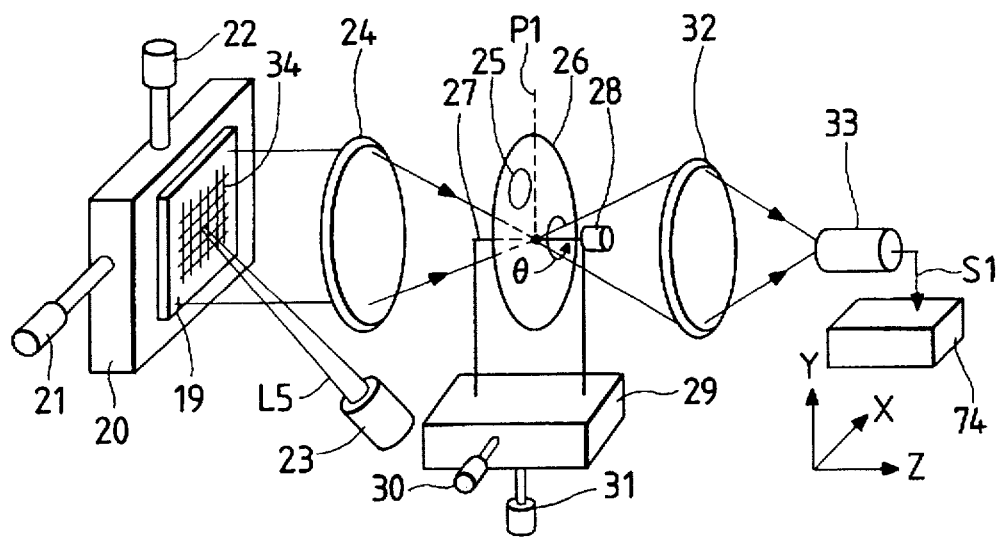
FIG. 5A is a perspective view depicting a construction of a mechanism of the particle inspecting apparatus in a first embodiment of the present invention.

FIG. 5A illustrates a mechanism of a particle inspecting apparatus in this embodiment. Referring to FIG. 5A, an object 19 to be inspected is fixedly supported on a table stage 20 movable in X- and Y-directions orthogonal to each other. Driving units 21, 22 move the table in the X- and Y-directions. Then, with a movement of the table 20, the inspected object 19 is moved in the X- and Y-directions. A beam of light L5 emitted from a light source 23 is obliquely incident on the inspected object 19. The beam L5 may be arranged to fall on the inspected object 19 perpendicularly from the surface or fall thereon from the rear surface. In this case, the inspected object 19 and the beam L5 can be relatively moved with the movement of the table 20. Further, the driving units 21, 22 are capable of rotating the table 20.

A light receiving lens 24 is disposed in a Z-direction perpendicular to the surface of the inspected object 19. A light intercepting plate 26 formed with an aperture 25 is provided on or in the vicinity of a pupil plane (Fourier transform plane) P1 of the light receiving lens 24. This is equivalent to such an arrangement that the light intercepting plate 26 is installed on the Fourier transform plane, wherein f is the focal length of the light receiving lens 24, and following two distances are equally set to f, one distance extending from the inspected object 19 to a principal point of the light receiving lens 24, another distance extending from the principal point of the light receiving lens 24 to the light intercepting plate 26. The light intercepting plate 26 is rotatable about a driving shaft 27 in a θ-direction by means of a driving unit 28. Further, the light intercepting plate 26 is so supported on a stage 29 as to be movable in the X- and Y-directions through driving units 30, 31. A position of the aperture 25 is freely shiftable in the X- and Y-direction as well as in the rotating direction by the driving units 28, 30, 31.

Besides, a lens 32 and a photodetector 33 are sequentially disposed in such a direction that the lens 32, the photodetector 33 and the light receiving lens 24 are symmetrical with respect to the light intercepting plate 26. A light receiving surface of the photodetector 33 is located in a position conjugate to the light intercepting plate 26 and the aperture 25 through the lens 32. The beam passing through the aperture 25 is converged (imaged in reduction) at the light receiving surface of the photodetector 33 via the lens 32. Then, the beam incident on the photodetector 33 is photoelectrically converted by the photodetector 33. A detection signal S1 substantially proportional to a quantity of light traveling through the aperture 25 is outputted from the photodetector 33.

Figure 5B:
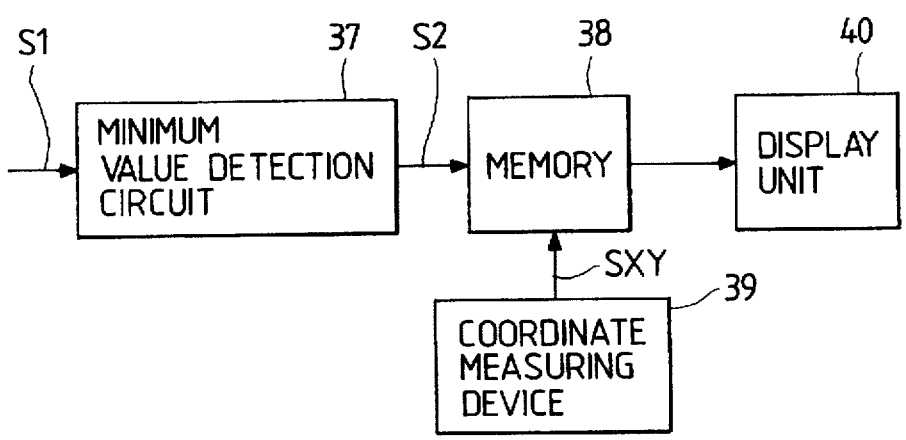
FIG. 5B is a block diagram illustrating a signal processing section in the first embodiment of the present invention.

FIG. 5B depicts a signal processing section in this embodiment. Paying attention to FIG. 5B, a minimum value detection circuit 37 is supplied with the detection signal S1 of the photodetector 33. A signal S2 corresponding to a minimum value detected by the minimum value detection circuit 37 is stored in a memory 36 vie, e.g., an unillustrated digital-to-analog converter. Besides, a coordinate measuring device 39 constructed of a linear encoder or the like detects X- and Y-coordinates of the stage 20 of FIG. 20. The memory 38 also stores coordinate information SXY corresponding to the X- and Y-coordinates of the stage 20. Contents stored in the memory 38 are displayed on a display unit 40 at any time. The minimum value detection circuit 37, the memory 38 and the coordinate measuring device 39 are provided inwardly of a main control system 74. Further, the main control system 74 controls the whole apparatus in a generalizing manner as well as actuating the driving units 21, 22, 28, 30, 31.

Given next is an explanation of one example of a particle detecting action by the particle inspecting apparatus in this embodiment.

Referring first to FIG. 5A, in a state where X- and Y-directional positions of the stage 20 holding the inspected object 19 are fixed, the beam L5 falls spot-wise on the inspected object 19. At this time, if particles such as dusts exist together with an original pattern 34 on the inspected object 19, optical information of the particles is generated in the form of diffracted light and/or scattered light. The thus generated optical information is Fourier-transformed by the light receiving lens 24, whereby a Fourier transform image is formed on the light intercepting plate 26 (pupil plane). On this occasion, the driving unit 28 is actuated to cause one rotation of the light intercepting plate 26 in the θ-direction. Subsequently, X- and Y-directional positions of the stage 29 are shifted by operating the driving shafts 30, 31, thus shifting the position of the aperture 25. When gradually shifting the position of the stage 29 in this manner, the X- and Y-directional coordinates of the stage 29 are respectively given such as: $(X_1, Y_1), (X_2, Y_2), \ldots, (X_i, Y_i), \ldots, (X_n, Y_n)$.

Figure 6A:
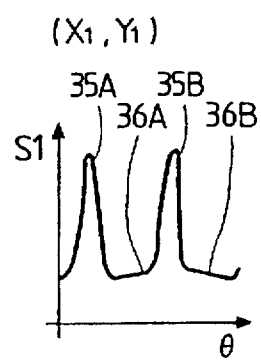
FIG. 6A is a waveform diagram showing one example of a variation in a detection signal S1 versus a rotational angle $\theta$ wherein $(X_1, Y_1)$ are the coordinates of a stage 29.
Figure 6B:
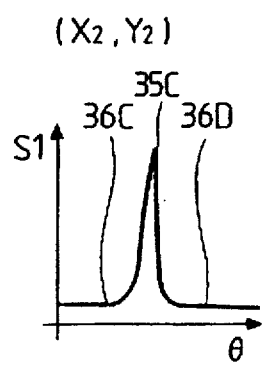
FIG. 6B is a waveform diagram showing one example of the variation in the detection signal S1 versus the rotational angle $\theta$ wherein $(X_2, Y_2)$ are the coordinates thereof.
Figure 6C:
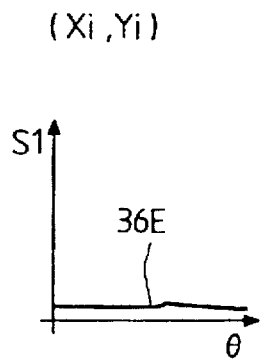
FIG. 6C is a waveform diagram showing one example of the variation in the detection signal S1 versus the rotational angle $\theta$ wherein $(X_i, Y_i)$ are the coordinates thereof.

The detection signal S1 of the photodetector 33 that is obtained at that time turns out as shown in FIGS. 6A–6C, wherein the parameters are a rotational angle (indicated by θ) of the aperture 25 in the θ-direction and coordinates $(X_i, Y_i)$ of the stage 29. More specifically, FIG. 6A shows one example of the detection signal S1 when the aperture 25 rotates in the θ-direction with the coordinates of the stage 29 being $(X_1, Y_1)$. Similarly, FIGS. 6B and 6C each show one example of the detection signal S1 when the aperture 25 rotates in the θ-direction with the coordinates of the stage 29 being $(X_2, Y_2)$ and $(X_i, Y_i)$, respectively. Corresponding to variations both in the rotational angle θ and in the coordinates $(X_i, Y_i)$, a beam spot of the Fourier transform image of the pattern 34 passes through the aperture 25 of FIG. 5A, and this beam reaches the photodetector 33. At this time, there can be seen increments in the detection signals S1 as depicted by peaks 35A, 35B, 35C of FIGS. 6A and 6B. On the other hand, if the beam spot of the Fourier transform image of the pattern 34 does not pass through the aperture 25, low-level detection signals S1 as depicted by levels 36A, 36B, 36C, 36D, 36E of FIGS. 6A–6C are obtained with almost no variation in the quantity of scattered light traveling through the aperture 25. These signals serve as optical information from the particles which does not contain the information of the diffracted light of the pattern 34. It is desirable that a size of the aperture 25 be smaller than an interval between the after the Fourier transform beam spots on the Fourier transform plane P1.

Then, the particles are detected by the signal processing circuit of FIG. 5B. Turning to FIG. 5B, the detection signals S1 of the photodetector 33 of FIG. 5A are inputted to the minimum value detection circuit 37. Detected consequently is a signal S2 corresponding to the minimum value of the detection signal S1 when varying the rotational angle θ and the coordinates $(X_i, Y_i)$ as the parameters. This signal S2 is stored in the memory 38. Simultaneously, the coordinate measuring device 39 monitors the X- and Y-directional coordinates (X, Y) of the stage 29 folding the inspected object 19 of FIG. 5A at that time. The coordinate information SXY outputted from the coordinate measuring device 39 is also stored in the memory 38. An irradiation area of the beam L5 is set smaller than an inspection area. Hence, the detection signals S1 are measured while varying the rotational angle θ and the coordinates $(X_i, Y_i)$. Thereafter, eventually the entire surface of the inspected object 19 is scanned by the beam L5 by moving the table 20 of FIG. 5A. Displayed subsequently on the display unit 40 of FIG. 5B are X- and Y-directional positions of the cluster of particles on the inspected object 19 and a value of the signal S2 corresponding to the minimum value.

When displayed on the display unit 40, the coordinates (X, Y) of the stage 20 and the value of the signal S2 may be displayed in the form of a table. However, for instance, they may also be displayed two-dimensionally as a map in accordance with a configuration of the inspected object 19. The respective particles may be displayed as points on the map in accordance with the coordinates (X, Y) when detecting the particles. In this case, a large size of particles result in an increase in terms of quantity of the scattered light. Accordingly, if the level of the signal S2 corresponding to the minimum value is large, the particles are judged to be large. Thus, a point size on the map is changed correspondingly to a magnitude of the signal S2. Alternatively, degrees of the particles are expressed by use of alphabetic letters A, B, C, wherein, for example, C implies a large size of particles, B is a middle size of particles, and A is a small size of particles. Moreover, indications separated by color may be given by use of a CRT color display unit. Further, a method of giving indications with variations in gradation through a CRT monochrome display unit is also effective.

In addition, when detecting the particle by the above-mentioned method, it may happen that optical information on something different from either the pattern or the particles is obtained. As this example, there may be given flare light coming from the optical system and stray light generated when the beam L5 is reflected by a constructional unit (e.g., the stage 20) other than the inspected object 19. For preventing a misdetection thereof, a comparator (not shown) is provided between the minimum value detection circuit 37 and the memory 38 of FIG. 5B. The extremely small signals S2 may be eliminated by this comparator.

Figure 7A:
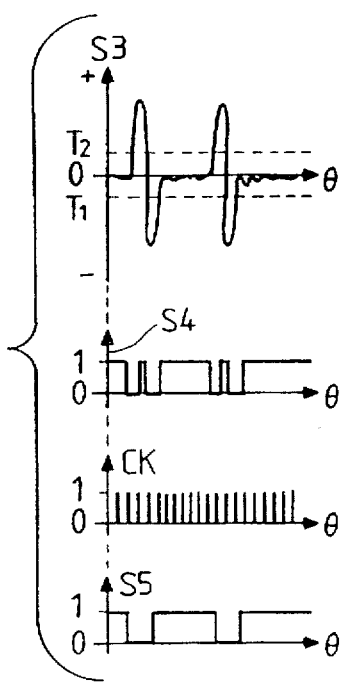
FIG. 7A is a waveform diagram showing a signal and a clock pulse that are obtained when processing the detection signal S1 of FIG. 6A.
Figure 7B:
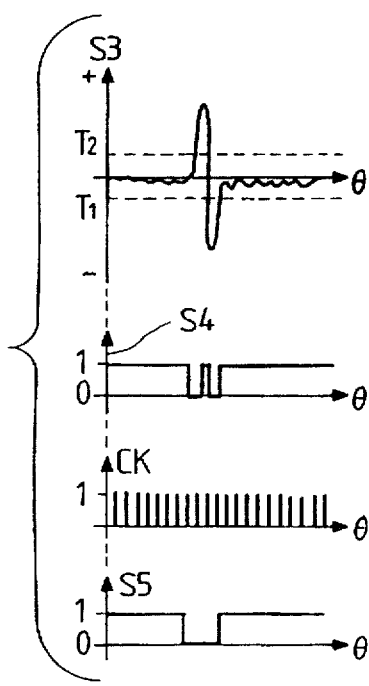
FIG. 7B is a waveform diagram showing a signal and a clock pulse that are obtained when processing the detection signal S1 of FIG. 6B.
Figure 7C:
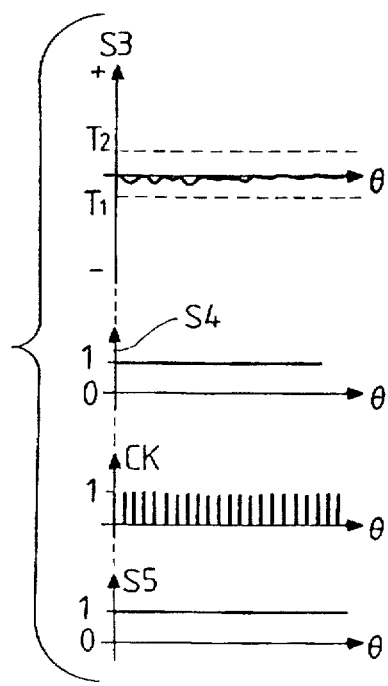
FIG. 7C is a waveform diagram showing a signal and a clock pulse that are obtained when processing the detection signal S1 of FIG. 6C.

Another method of obtaining particle signals out of the detection signals S1 of FIG. 5A will be explained with reference to FIGS. 7A–7C. FIGS. 7A, 7B, and 7C corresponding respectively to FIGS. 6A, 6B and 6C. Further, referring to FIGS. 7A–7C, a signal is obtained by differentiating the detection signal S1 of FIG. 5A with the rotational angle θ. The signal S3 assumes a high-level "1" when existing between threshold values $T_1$ and $T_2$ but assumes a low-level "0" when in others. Digitalization is performed to attain this, thereby obtaining a signal S4. The signal S4 becomes the high-level "1" at the levels 36A, 36B, 36C, 36D, 36E and at the peaks 35A, 35B, 35C.

Paying attention to FIGS. 7A–7C, a clock pulse CK is a pulse (defined as an output signal of a rotary encoder provided in, e.g., the driving unit 28) generated corresponding to the rotational angle θ of the light intercepting plate 26 of FIG. 5A. A signal S5 is so obtained as to assume the high-level "1" when a width of the high-level "1" portion of the signal S4 is equal to or greater than a predetermined number of pulses on the basis of the clock pulse CK but assume the low-level "0" in other portions. The signals S5 of FIGS. 7A–7C become "1" corresponding to only the levels 36A, 36B, 36C, 36D, 36E of FIGS. 6A–6C. It therefore follows that the particle information is indicated when the signal S5 is at the level "1".

Then, a signal quantity when the signal S5 assumes the level "1" and when a signal value of the detection signal S1 is minimum or maximum is treated as a piece of information indicating a size of the cluster of particles in the same way with the signal S2 of FIG. 5B. The same processing as that in FIG. 5B is conducted. In the signal processing section of FIG. 5B. only the maximum value among the levels 36A, 36B, 36C, 36D, 36E of FIGS. 6A–6C can be known. Contrastingly, according to the processing method shown in FIGS. 7A–7C, there can be known the maximum value of the detection signal S1 and further a mean value of the detection signal S1. The advantage is that the particle information exhibiting a higher correlation with respect to the particle size is to be obtained.

Note that the stage 20 in the embodiment illustrated in FIG. 5A is constructed to be movable X- and Y-directions with the aid of the driving units 21, 22. A purpose of moving the stage 20 is, however, to sequentially scan the entire surface of the inspected object 19 by using the beam L5. Accordingly, it is enough to change a relativity between the irradiation position of the beam L5 and the position of the inspected object 19. Hence, the stage 20 is moved in the Y-direction by only the driving unit 22. The beam L5 is deflected by a scanner mirror (e.g., a galvano-scanner mirror and a polygon scanner mirror). The inspected object 19 may be scanned by the deflected beam L5 in the X-direction thereof. The driving unit 21 can be thereby removed, and, besides, the entire surface of the inspected object 19 can be scanned by the beam L5 at a higher speed.

Figure 8:
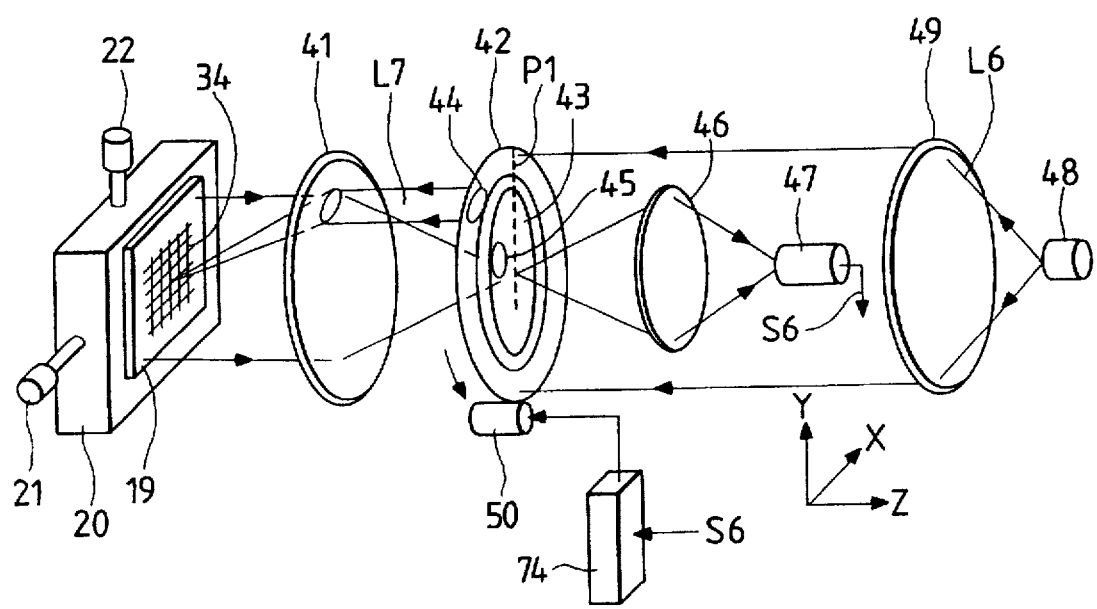
FIG. 8 is a perspective view illustrating a construction of the mechanism in a second embodiment of the present invention.

Next, a second embodiment of the present invention will be discussed with reference to FIG. 8. Referring to FIG. 8, the portions corresponding to those in FIG. 5A are marked with the like numerals, and the detailed explanation thereof will be omitted.

FIG. 8 illustrates a mechanism of the particle inspecting apparatus in this embodiment. In FIG. 8, the inspected object 19, the stage 20 and the driving units 21, 22 have the same constructions as those in the embodiment of FIG. 5A. In accordance with this embodiment, a light receiving lens 41 is disposed in the Z-direction perpendicular to the inspected object 19. A ring-like intercepting plate 42 and a disk-like light intercepting plate 43 substantially inscribed in this light intercepting plate 42 are provided substantially on the pupil plane (corresponding to an arrangement plane of the light intercepting plate 26 of FIG. 5A) of the light receiving lens 41. The light intercepting plates 42, 43 are formed with apertures 44, 45.

A lens 46 and a photodetector 47 are sequentially arranged in such a direction that the lens 46, the photodetector 47 and the light receiving lens 41 are symmetrical with respect to the light intercepting plates 42, 43. A light receiving surface of the photodetector 47 is disposed in a position conjugate to the light intercepting plate 43 through the lens 46. A signal S6 substantially proportional to a quantity of light received is outputted from the photodetector 47. Further, a light of beam L6 emitted from a light source 48 is substantially collimated by a condenser lens 49 and reaches the light intercepting plate 42. A light of beam L7 passing through the aperture 44 of the light intercepting plate 42 falls on the inspected object 19 via the light receiving lens 41. The light intercepting plate 42 in this embodiment assumes an annular band in its external configuration. A driving unit 50 is so provided as to be contiguous to the outer periphery of the light intercepting plate 42. The light intercepting plate 42 is constructed to be rotatable in the θ-direction, i.e., in the peripheral direction with the aid of the driving unit 50.

Now, rotating the light intercepting plate 42 in the θ-direction (the rotational angle is also set at θ) by the driving unit 50, an incident vector when the beam L7 is incident on the inspected object 19 varies in accordance with the rotational angle θ. Accordingly, there shifts a relative position, versus the aperture 45, of the Fourier transform image of the pattern 34 on the inspected object 19 in conformity with the principle which has already been stated. Hence, it follows that the detection signal S6 of the photodetector 47 in relation to the optical information which is incident on the photodetector 47 via the aperture 45 takes the same behaviors as those of the detection signal S1 of FIGS. 6A, 6B or 6C. The detection principle explained in the embodiments of FIGS. 5A and 5B can be utilized substantially as it is. The only difference therebetween is that the parameter is nothing but the rotational angle θ. The detection principle in the embodiments of FIGS. 5A and 5B can be, however, substantially applied by combining the embodiments of FIGS. 5A and 5B, i.e., by moving both of the apertures 44 and 45. This produces such an advantage that the photodetector 47 is capable of obtaining a much larger amount of optical information. Note that the main control system 74 processes the detection signal S6 and at the same time generalize-controls the whole of other devices for controlling the respective driving units.

Next, a third embodiment of the particle inspecting apparatus according to the present invention will be explained with reference to FIGS. 9 and 10. The explanation will be given by marking the same members as those in FIGS. 5A, 5B and 8 with the like numerals.

Figure 9A:
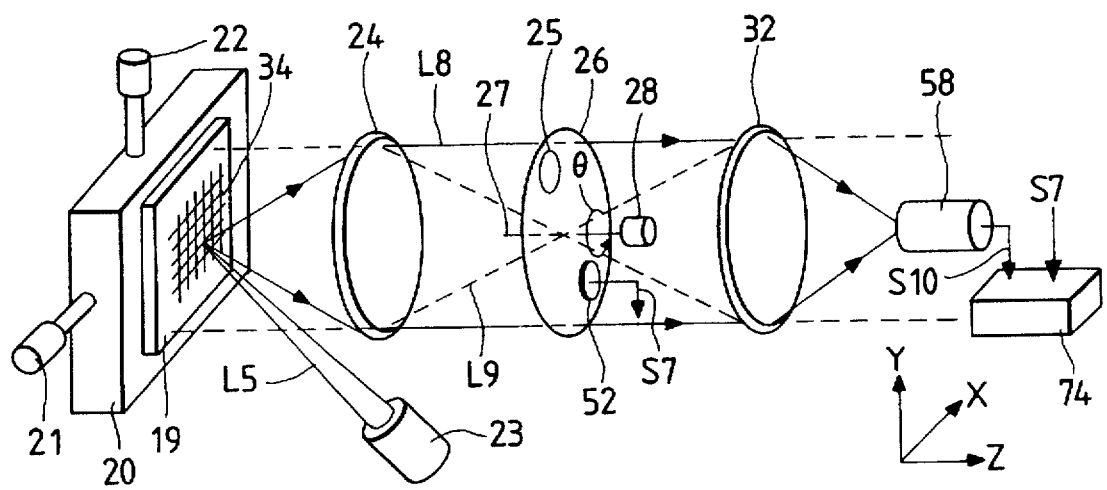
FIG. 9A is a perspective view illustrating a construction of the mechanism of the particle inspecting apparatus in a third embodiment of the present invention.
Figure 10:
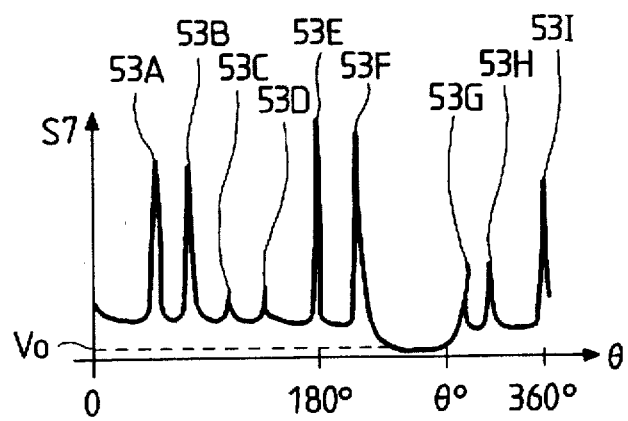
FIG. 10 is a waveform diagram showing one example of a variation in a detection signal S7 versus the rotational angle $\theta$ in the embodiment of FIG. 9A.

FIG. 9A illustrates a mechanism of the particle inspecting apparatus in the third embodiment. Referring to FIG. 9A, the inspected object 19 is fixedly supported on the table stage 20 movable in the X- and Y-directions orthogonal to each other. The stage 20 and the inspected object 19 can be moved by the driving units 21, 22 in the X- and Y-directions. The beam L5 emitted from a light source 3 is obliquely incident on the inspected object 19. The beam L5 may be arranged to fall on the inspected object 19 perpendicularly from the surface or fall thereon from the rear surface. Further, the table 20 is rotatable by the driving units 21, 22. The light receiving lens 24 is disposed in the Z-direction perpendicular to the surface of the inspected object 19. The light intercepting plate 26 formed with the aperture 25 is provided on or in the vicinity of the pupil plane (Fourier transform plane) of the light receiving lens 24. This is equivalent to such an arrangement that the light intercepting plate 26 is disposed on the Fourier transform plane, wherein f is the focal length of the light receiving lens 24, and following two distances are equally set to f, one distance extending from the inspected object 19 to the principal point of the light receiving lens 24, another distance extending from the principal point of the light receiving lens 24 to the light intercepting plate 26. The light intercepting plate 26 is so supported as to be rotatable about the driving shaft 27 in the θ-direction by means of the driving unit 28.

Figure 9B:
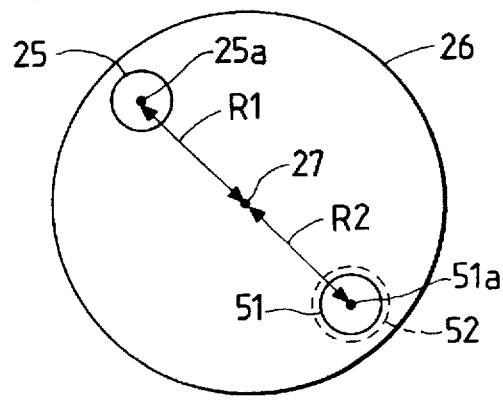
FIG. 9B is a front view of a light intercepting plate 26 as viewed from a light receiving lens 24 in the third embodiment of this invention.

Further, FIG. 9B of the light intercepting plate 26 as viewed from the light receiving lens 24 in the Z-axis direction. As illustrated in FIG. 9B, a second aperture 51 is formed in a position on the light intercepting plate 29 so that the aperture 51 and the aperture 25 are symmetrical with respect to the driving shaft 27. A photodetector 52 is closely fixed to the rear surface of the second aperture 51. Namely, a distance R1 from the driving shaft 27 to a center 25a of the aperture 25 is equal to a distance R2 from the driving shaft 27 to a center 51a of the aperture 51. The aperture centers 25a, 51a are out of phase 180° with respect to a rotation about the driving shaft 27. The photodetector 52 photoelectrically converts the beam of light traveling via the light receiving lens 24 and the aperture 51 of the light intercepting plate 26 among the beams of light coming from the inspected object 19, thereby outputting a detection signal S7.

Turning to FIG. 5A, the lens 32 and an imaging device 58 such as a two-dimensional charge coupled device (two-dimensional CCD) are sequentially arranged in such a direction that the lens 32, the imaging device 58 and the light receiving lens 24 are symmetrical with respect to the light intercepting plate 26. An imaging surface of the imaging device 58 is disposed on a plane conjugate to the inspected object 19 through the light receiving lens 24 and the lens 32 as well. More specifically, the imaging device 58 images a conjugate image of the inspected object 19 in combination with the light traveling from the inspected object 19 via the light receiving lens 24, the aperture 25 and the lens 32. The imaging device 58 thereby outputs an imaging signal S10. FIG. 9A shows a conjugate relationship between the inspected object 19 and the imaging device 58 through a light path L8 indicated by the solid lines. FIG. 9A also shows beams of the pupil plane through a light path L9 indicated by the broken lines. Note that in this embodiment also, the main control system 74 processes the detection signal S7 and the imaging signal S10 and at the same time generalize-controls the whole of other devices for controlling the respective driving units.

Given next is an explanation of a particle detecting operation by the particle inspecting apparatus in this embodiment.

Paying attention to FIG. 9A, in a state where the X- and Y-directional positions of the stage 20 are fixed, the beam L5 falls spotwise on the inspected object 19. At this time, optical information of the original pattern 34 on the inspected object 19 and the optical information, if particles such as dusts exist on the inspected object 19, are generated in the form of diffracted light and/or scattered light. A fourier transform image of the thus generated light through the light receiving lens 24 is formed on the light intercepting plate 26 (on the pupil plane). At this moment, the driving unit 28 is actuated to cause one rotation of the light intercepting plate 26 in the θ-direction.

On this occasion, the photodetector 52 outputs the detection signal proportional to a quantity of light received. The detection signal S7 thereof changes as shown in FIG. 10 with respect to a rotational angle (indicated by θ) in the θ-direction. Then, as depicted in FIG. 10, peaks 53A, 53B, ....53I are present in the detection signal S7 corresponding to a timing at which the beam spot of the Fourier transform image of the diffracted light from the pattern 34 of FIG. 9A falls on the photodetector 52 via the aperture 51 (see FIG. 9B). At rotational angles θ other than the above-mentioned, however, the diffracted light from the pattern 34 on the inspected object 19 does not enter the aperture 52. Particularly at a rotational angle $θ_0$ of FIG. 10, the detection signal S7 turns out a minimum output $V_0$. Almost no diffracted light from the original pattern enters the aperture 51 at the rotational angle $θ_0$. If the particles exist, only the optical information from the particles, it can be conceived, come in the aperture 51.

Then, as shown in FIG. 9B, the apertures 25, 51 are out of phase 180° with respect to the rotational angle θ. Utilizing this fact, the rotational angle θ of the light intercepting plate 26 is fixedly set at ($θ_0$+180°) by means of the driving unit 28. The optical information passing through the aperture 25 of the light intercepting plate 26 becomes identical with the optical information passing through the aperture 51 when the rotational angle θis $θ_0$.

At that time, the imaging device 58 images a conjugate image of the inspected object 19 in combination with the light traveling via the aperture 25, viz., an image of only the particles on the inspected object 19. An imaging signal of the imaging device 58 is supplied to an unillustrated monitor image receiver or the like. The image of the particles can be displayed on the monitor image receiver. The particle image may be, however, visually viewed by use of an eyepiece instead of employing the imaging device 58.

After an end of the above-mentioned operation, the stage 20 is properly moved stepwise in the X- and Y-directions by the driving units 21, 22. The entire surface of the inspected object 19 is thus inspected by the beam L5. After finishing the inspection on the entire surface of the inspected object 19, particle positions on the inspected object 19 may be automatically displayed through a two-dimensional map. In this instance, a minimum value $V_0$ of the detection signal S7 with respect to the rotational angle θ is detected in given X- and Y-directional positions of the stage 20. When the minimum value $V_0$ falls within a given range, it is automatically judged that there exist particles. This operation is repeated sequentially while shifting the X- and Y-directional positions of the stage 20. The X- and Y-directional positions when detecting the particles are measured by an unillustrated measuring device (e.g., an linear encoder, etc.) provided on the stage 20. There are thus known an existence or non-existence of the particles and obtained, if the particles are present, X- and Y-directional coordinates of the particles. A particle distribution can be displayed by the two-dimensional map.

Separately from this, an SN ratio of the imaging signal S10 of the imaging device 58 may be improved by use of a image processing means. Even when the light intercepting plate 26 is set at such a rotational angle that the diffracted light passing through the aperture 25 is minimized, the diffracted light, though feeble, contains the information about the diffracted light of the original pattern 34. Excepting an intensive-light-quantity particle image, a feeble-light-quantity image of the pattern 34 is therefore superposed on the image obtained by the imaging device 58. Hence, only the information of the particle image is obtained from the imaging signal 10 by imaging processing (such as e.g., filtering and differentiating). Only the particles can be thereby accurately detected.

Further, the photodetector 52 is provided in FIG. 9A. An integral value of the output signals of all the pixels of the imaging device 58 is the same signal as the detection signal S7 of the photodetector 52 thereof. The phase is, however, shifted 180°. Hence, an integration circuit of the output signals of all the pixels of the imaging device 58 can substitute for the photodetector 52. If the photodetector 52 is thus omitted, the configuration of the optical system can be more simplified.

Figure 11:
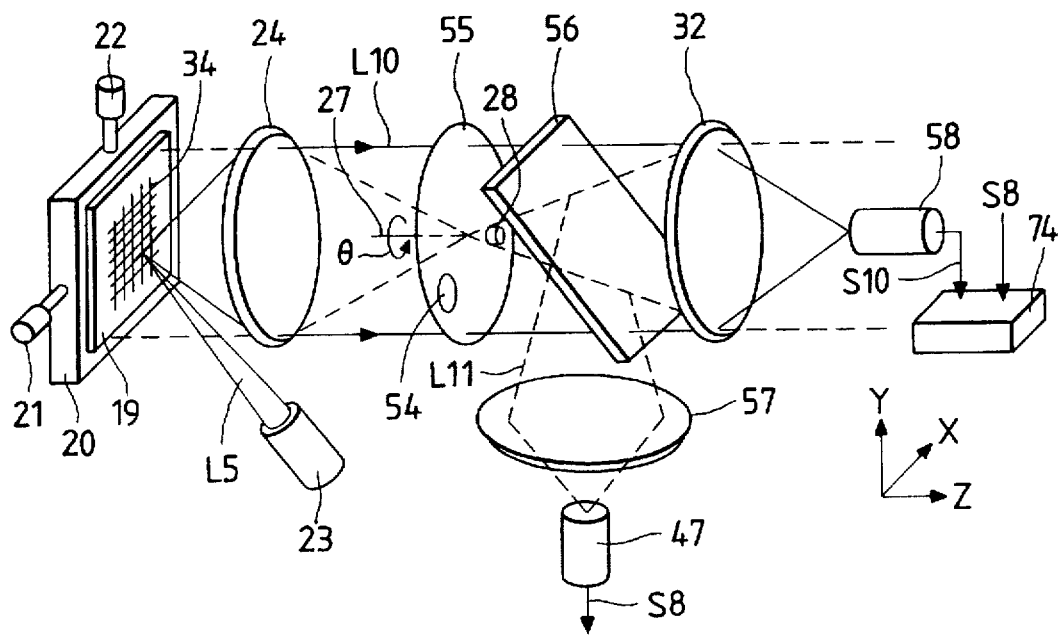
FIG. 11 is a perspective view depicting a construction of the mechanism of the particle inspecting apparatus in a fourth embodiment of this invention.

Next, a fourth embodiment of the present invention will be discussed with reference to FIG. 11. Referring to FIG. 11, the portions corresponding to those in FIG. 9A are marked with the same numerals, and their explanations will be omitted. In the fourth embodiment, however, the inspected object 19, the stage 20, the driving units 21, 22, the light source 23, the light receiving lens 24, the lens 32 and the imaging device 58 are all the same as those in the third embodiment of FIG. 9A.

Turning to FIG. 11, a light intercepting plate 55 having an aperture 54 is disposed in the same position as the light intercepting plate 26 of FIG. 9A, i.e., on the pupil plane of the light receiving lens 24. A half-mirror 56 is disposed between the light intercepting plate 55 and the lens 32. The light passing through the aperture 54 is taken out through the half-mirror 56. The thus taken-out light is converged (imaged in reduction) at the light receiving surface of the photodetector 47 via a lens 57. In this case, the light receiving surface of the photodetector 47 is disposed in a position conjugate to the light intercepting plate 55 through the lens 57. Outputted from a photodetector 58 is a detection signal S8 substantially proportional to a quantity of the light traveling through the aperture 54. To be specific, in FIG. 11, a solid-line light path L10 indicates a conjugate relationship between the inspected object 19 and the imaging device 58. A broken-line light path L11 indicates a conjugate relationship between the light intercepting plate 55 on the pupil plane and the photodetector 47.

The light intercepting plate 55 is also rotatable about the driving shaft 27 in the θ-direction by means of the driving unit 28, wherein a rotational angle is indicated by θ. Then, it follows that the photodetector 47 receives the light having a quantity proportional to the optical information passing through the aperture 54. A detection signal S8 is therefore absolutely analogous to the detection signal S7 of FIG. 10. Besides, the rotational angle $θ_0$ of the light intercepting plate 26 when the detection signal S7 of the photodetector 52 is minimized and the rotational angle of the light intercepting plate 26 when the quantity of light passing through the aperture 25 is minimized are out of phase 180° in the third embodiment. Contrastingly, in the fourth embodiment of FIG. 11, the quantity of light traveling through the aperture 54 is minimized when the detection signal S8 of the photodetector 58 is minimized. Accordingly, as in the same way with the third embodiment, only the particles can be viewed by the imaging device 58 simply by setting the rotational angle of the light intercepting plate 55 in such a state that this detection signal S8 is minimized. Note that in this embodiment also, the main control system 74 processes the detection signal S8 and the imaging signal S10 and at the same time generalize-controls the whole of other devices for controlling the respective driving units.

Figure 12:
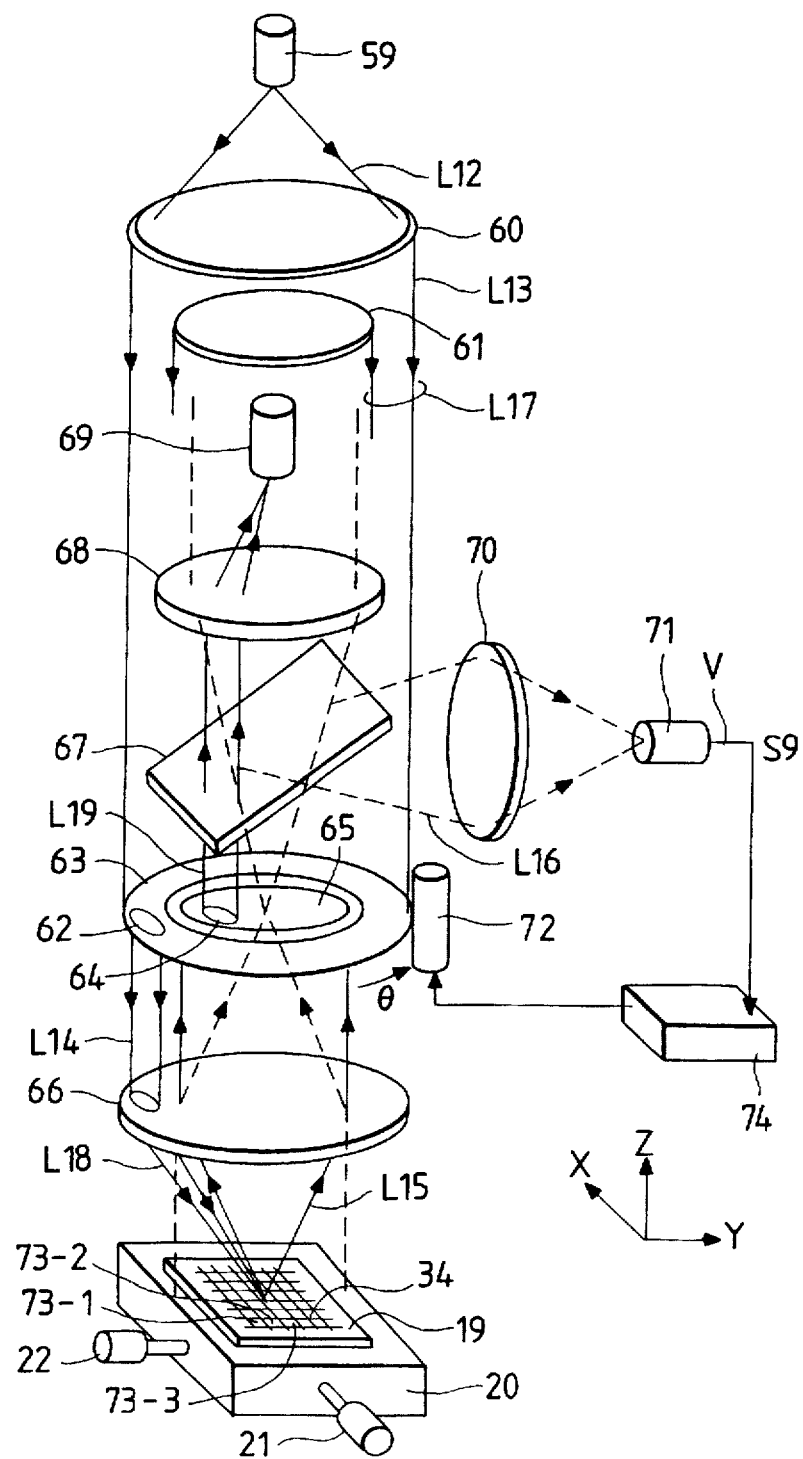
FIG. 12 is a perspective view depicting a construction of the mechanism of the particle inspecting apparatus in a fifth embodiment of this invention.

Next, a fifth embodiment of the present invention will be discussed with reference to FIG. 12. The portions corresponding to those in FIG. 9A are marked with the same numerals. Turning to FIG. 12, the inspected object 19 formed with the original pattern 34 is placed on the stage 20. The stage 20 and the inspected object 19 are movable in the X- and Y-directions by the driving units 21, 22. The driving units 21, 22 are also capable of rotating the stage 20.

Referring to FIG. 12, a beam of light L12 emitted from a light source 59 is substantially collimated into a beam of light L13 through a lens 60. However, a circular light intercepting plate 61 is disposed in such a direction that the light source 59 and the light intercepting plate 61 are symmetrical with respect to the lens 60. The light outgoing from the lens 60 turns out a beam of annular-band illumination light L17 and falls on an annular-band light intercepting plate 63 formed with an aperture 62. A major diameter of the beam of annular-band illumination light L17 is substantially equal to or a slightly smaller than a major diameter of the annular-band light intercepting plate 63. A minor diameter of the beam of annular-band illumination light L17 is substantially equal to or slightly larger than a minor diameter of the annular-band light intercepting plate 63.

A beam of light L14 passing through an aperture 62 of the annular-band light intercepting plate 63 turns out a beam of light L18 through a light receiving lens 66 and is obliquely incident on the inspected object 19. Beams of light L15 such as diffracted light and scattered light generated from the inspected object 19 are condensed by the light receiving lens 66. The condensed light travels through an aperture 64 formed in a circular light intercepting plate 65 disposed on the pupil plane (Fourier transform plane of through the light receiving lens 66 for the inspected object 18) of the light receiving lens 66. Positions of the light intercepting plate 65 and the aperture 64 are fixed. The arrangement that the light intercepting plate 65 is disposed on the pupil plane of the light receiving lens 66 is equivalent to such an arrangement that the light intercepting plate 65 is disposed on the Fourier transform plane, wherein f is the focal length of the light receiving lens 66, and following two distances are equally set to f, one distance extending from the inspected object 19 to the principal point of the light receiving lens 66, another distance extending from the principal point of the light receiving lens 66 to the light intercepting plate 65. Further, in accordance with this embodiment, the circular light intercepting plate 65 is so disposed as to be substantially inscribed in the annular-band light intercepting plate 63. Note that the aperture 64 may be rotated or further moved in translation.

A half-mirror 67, a lens 68 and an imaging device 69 such as a two-dimensional CCD are arranged sequentially from the light intercepting plate 65 toward the circular light intercepting plate 61. A lens 70 and a photodetector 71 are disposed in such a direction that the light from the aperture of the light intercepting plate 65 is reflected by the half-mirror 67. In this instance, a part of beams of light passing through the aperture 64 of the light intercepting plate 65a penetrates the half-mirror 67. This beam of light is then imaged as a two-dimensional image on the imaging surface of the imaging device 69 disposed in a position conjugate to the inspected object 19 through the lens 68. The conjugate image of the inspected object 19 may be visually viewed through an eyepieces disposed in place of the imaging device 69.

On the other hand, a beam of light L16 among the beams of light passing through the aperture 64 of the light intercepting plate 65 is reflected by the half-mirror 67. The beam L16 is converged through the lens 70 at the light receiving surface of the photodetector 71 provided in a position conjugate to the aperture 64 on the pupil plane. Namely, the light receiving surface of the photodetector 71 is conjugate to the aperture 64. A light quantity proportional to the light traveling through the aperture 64 is photoelectrically converted by the photodetector 71. Further, the annular-band light intercepting plate 63 is so supported as to be rotatable in the θ-direction (its rotational angle is also indicated by θ), i.e., in the peripheral direction by means of a driving unit 72. Note that the aperture 62 may be moved in translation (in the X- and Y-directions).

In this fifth embodiment, when rotating the annular-band light intercepting plate 63 in the θ-direction (its rotational angle is also indicated by θ) by actuating the driving unit 72, an incident vector of the beam L14 on the inspected object 19 varies. Consequently, there changes a relative position relationship between the aperture 64 of the light intercepting plate 65 and the Fourier transform image of the pattern 34. Hence, a detection signal S9 that is the same as the detection signal S9 of FIG. 10 is obtained from the photodetector 71. It is possible to view only the particles by use of the imaging device 69 absolutely in the same way with the fourth embodiment.

Note that in this embodiment also, the main control system 74 processes the detection signal S9 and the imaging signal from the imaging device 69. The main control system 74 also controls the whole apparatus in the generalized manner as well as controlling the respective driving units.

A sixth embodiment of this invention will next be discussed with reference to a flowchart of FIG. 13 in combination with the construction of the apparatus depicted in FIG. 12. This embodiment deals with an arrangement wherein a relative position between the aperture and the Fourier transform image is shifted on the pupil plane of the light receiving lens by changing the direction of the incident vector on the inspected object. The present invention is, however, applicable similarly to a case where the aperture position is shifted while the direction of the incident vector is fixed.

In accordance with the sixth embodiment, when rotating the annular-band light intercepting plate 63 in the θ-direction by actuating the driving unit 72 of FIG. 12, an incident vector of the beam L18 on the inspected object 19 varies continuously. Hence, there changes a relative position relationship between the aperture 64 of the light intercepting plate 65 and the Fourier transform image of the pattern 34 of the inspected object 19.

Accordingly, in the case of inspecting the particles in, e.g., a certain narrow field (illumination area) on the inspected object 19, the stage 20 is moved so that the field is irradiated with the beam L18. Thereafter, the annular-band light intercepting plate 63 makes one rotation in the θ-direction and fixed in the position through such a rotational angle θ that the detection signal S9 of the photodetector 71 is minimized. In this state, there exists no beam spot with a high-intensity Fourier transform image of the original pattern 34 on the inspected object 19 in the aperture 64 of the light intercepting plate 65. Among the beams passing through the aperture 64, a quantity of the beam coming from the particles on the inspected object 19 is Greater than that of the beam from the pattern 34. Therefore, when viewing the conjugate image of the inspected object 19 through the imaging device 69 by use of the beams passing through the aperture 64, it is possible to clearly view the in-field particles on the inspected object 19.

In this case also, however, the quantity of beam from the pattern 34 is not 0. The particle is hard to view. Therefore, the SN ratio may be enhanced by effecting imaging processes such as a filtering process and a differentiating process on the imaging signal of the imaging device 69. Only the particles on the inspected object 19 can be thereby displayed as, e.g., luminant points on the CRT display unit. The particles can be detected more efficiently.

Further, in the case of inspecting the particles on the entire surface of the inspected object 19, it is assumed that optimum conditions are obtained by causing one rotation of the annular-band light intercepting plate 63 in the θ-direction in respective fields into which the entire surface thereof is finely partitioned. This results in an increase in the inspection time. Under such circumstances, this embodiment takes the following steps of reducing the inspection time.

There will next be explained the operation of this embodiment when inspecting the particles substantially over the entire surface of the inspected object 19 of FIG. 12. Herein, the explanation is given by exemplifying a means for changing the incident vector of the beam as a means for shifting the relative position between the Fourier transform image 13F (see FIG. 3A) and the aperture 64.

Figure 13:
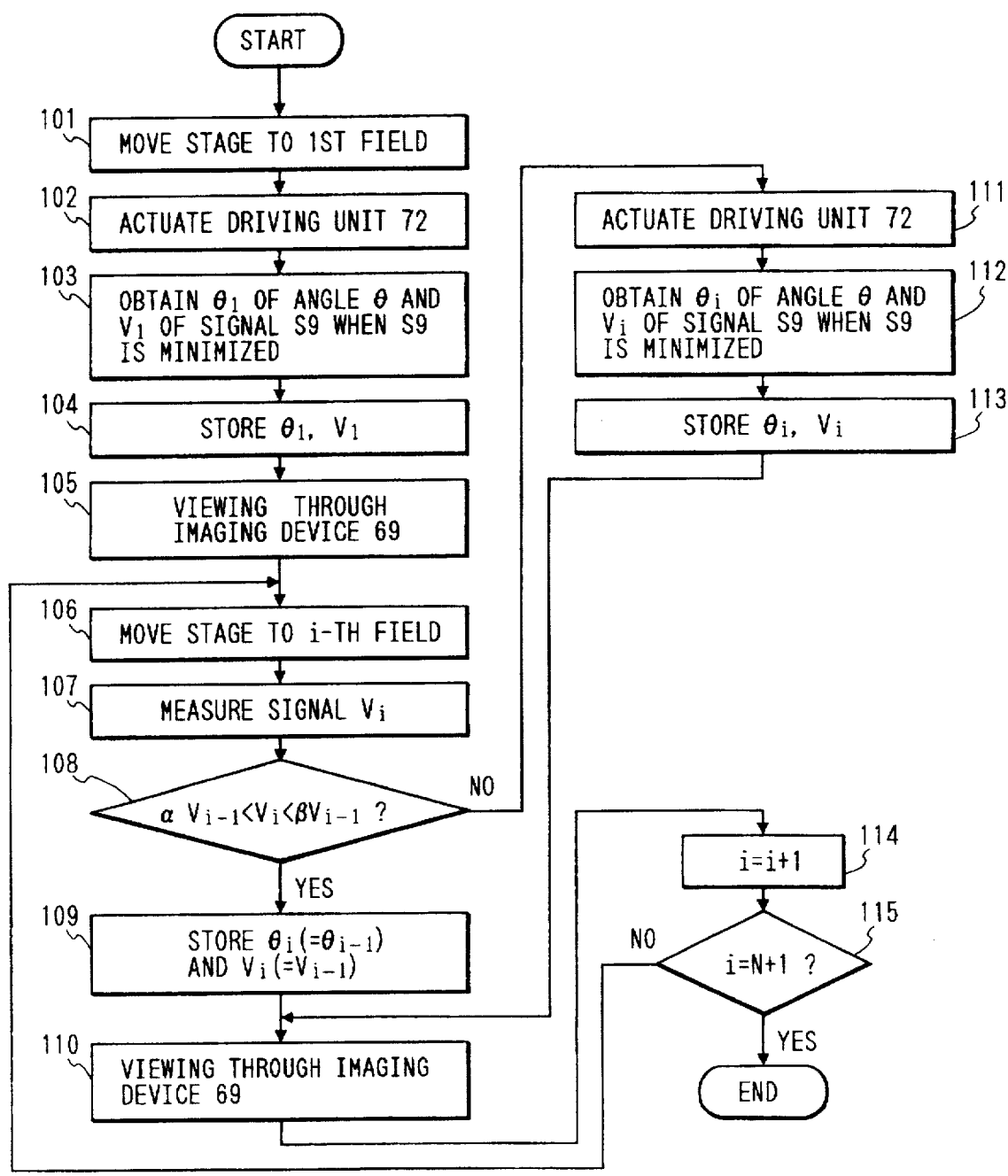
FIG. 13 is a flowchart showing one example of a particle inspecting operation in a sixth embodiment of this invention.

To start with, in step 101 of FIG. 13, the irradiation area of the beam L18 is set to a first field 73-1 on the inspected object 19 by operating the driving units 21, 22 of FIG. 12. Then, in step 102, the annular-band light intercepting plate 63 is caused to make one rotation in the θ-direction by operating the driving unit 72. Obtained next are a rotational angle $θ_1$ of the annular-band light intercepting plate 28 when the detection signal S9 of the photodetector 71 is minimized and a value $V_1$ of the detection signal S9 at that time (step 103). The rotational angle $θ_1$ and the value $V_1$ are stored as optimum aperture conditions of the first field 63-1 in a memory incorporated into the main control system 74 (step 104). Then, the rotational angle of the annular-band light intercepting plate 63 is fixed to $θ_0$. The particle in the first field 73-1 is viewed by means of the imaging device 69 (step 105).

Thereafter, in step 106, the irradiation area of the beam L18 is shifted to a second field 73-2 on the inspected object 19 by moving the stage 20. An initial value of an integer i is set to 2, and the second field 73-2 is generalized into an i-th field 73-i. In this case, the rotational angle of the annular-band light intercepting plate 63 is set to a rotational angle $θ_{i-1}$ used for viewing an (i−1)th field 73-(i−1). In a state of being at this rotational angle $θ_{i-1}$, the detection signal S9 of the photodetector 71 is measured, thereby obtaining a value $V_i$ (step 107). Next, let $V_{i-1}$ be a value stored as the detection signal S9 at the rotational angle $θ_{i-1}$ for the i-th field, and in step 108 the main control system 74 of FIG. 12 checks whether or not the following relationship is satisfied with respect to the value $V_{i-1}$ in which the value $V_i$ of this time is stored.

$$αV_{i-1} < V_i < βV_{i-1} \quad (1)$$

where the coefficient α is a smaller than 1, and β is a larger than 1. The coefficients α, β are set as follows:

$$α=0.9, β=1.1 \quad (2)$$

In this case, there is judged whether or not the value $V_i$ of the detection signal V in the i-th field coincides with the value $V_{i-1}$ stored as the detection signal S9 in the (i−1)th field within a range of ±10%.

If the formula (1) is satisfied as a result of this judgement, the action moves to step 109. Stored in the memory is the rotational angle $θ_{i-1}$ stored as the optimum aperture condition in the (i−1)th field, this rotational angle being defined as an optimum rotational angle $θ_i$ of the annular-band light intercepting plate 63 in the i-th field. Stored at the same time is the value $V_{i-1}$ stored as the detection signal V in the (i−1)th field as a value $V_i$ of the detection signal V under the optimum aperture condition in the i-th field. This is expressed such as:

$$θ_i = θ_{i-1}, V_i = V_{i-1} \quad (3)$$

Thereafter, the action moves to step 110. The particle in the i-th field 38-1 is viewed by the imaging device 69 in such a state that the rotational angle θ of the annular-band light intercepting plate 63 is set to the value $θ_{i-1}$ set in the (i−1)th field.

On the other hand, if the condition of the formula (1) is not satisfied in step 108, i.e., when $(V_i ≤ αV_{i-1})$ or $(βV_{i-1} ≤ V_i)$ is established, the action proceeds to step 111. The rotational angle of the aperture 62 of the annular-band light intercepting plate 63 is again optimized. More specifically, one θ-directional rotation of the annular-band light intercepting plate 63 is caused by operating the driving unit 72. Obtained thereafter in step 112 are the θ-directional rotational angle $θ_i$ of the annular-band light intercepting plate 63 when the detection signal S9 of the photodetector 71 is minimized. The value $V_i$ of the detection signal S9 at that time is also obtained.

Then, the memory is made to store the rotational angle $θ_i$ and the value $V_i$ as the optimum aperture conditions in the i-th field 73-i (step 113). Thereafter, in step 110, the rotational angle of the annular-band light intercepting plate 28 is fixed to the rotational angle $θ_i$ stored in step 113. The particle in the i-th field 73-i is viewed by the imaging device 69.

Note that in step 108, the action proceeds to step 111 only when, e.g., $(βV_{i-1} ≤ V_i)$ is established, and the aperture position may be shifted.

The action from step 110 proceeds to step 114, wherein there is judged whether or not the inspection of the next field on the inspected object 19 is to be conducted. More specifically, 1 is added to a value of variable i. After this step, whether or not the variable i reaches an integer (N+1) is checked in step 115. The integer N represents the number of fields obtained by partitioning the entire surface of the inspected object 19. Then, if the variable i does not reach the integer (N+1) in step 115, the action goes back to step 106, wherein the particle of the next i-th field on the inspected object 19 is inspected. Subsequently, (N−1) repetitions of the actions of steps 106 through 115 are performed. The particles in the fields 73-2, 73-3, . . . after the second field on the inspected object 19 are inspected. The inspections of the particles in the N-numbered fields on the inspected object 19 are thus ended.

As described above, according to this embodiment, after inspecting the particle in a k-th (k is a positive integer smaller than N) field on the inspected object 19, the particle in the (k+1)th field is to be inspected. On this occasion, the optimum aperture condition is not necessarily sought by rotating the annular-band light intercepting plate 63 in the θ-direction. Accordingly, the inspection time can be reduced down to a value smaller than by the inspection conducted while seeking the optimum aperture condition in each field. Particularly, when the original pattern 34 on the inspected object 19 is a periodic pattern, an intensity distribution of the Fourier transform image of the pattern 34 on the light intercepting plate 65 is substantially the same in the particle inspection in the k-th field or in the (k+1)th field. That is, if the pattern 34 is defined as the periodic pattern, the particles substantially in all the remaining fields can be inspected under the optimum aperture condition acquired for the first field on the inspected object 19. The time required for inspecting the particles on the entire surface of the inspected object 19 can be thereby remarkably reduced.

Note that in the embodiment discussed above, the optimization of the aperture 62 (or 64) involves the use of the output S9 given from the photodetector 71. However, whether or not the aperture position is shifted by use of the imaging signal from the imaging device 69 may be determined without providing the photodetector 71. At this time, there are employed values to which outputs per array of the imaging device, e.g., a CCD are added. With this arrangement, the imaging device 69 can serve as the photodetector 71, thereby simplifying the apparatus.

Further, in the embodiment discussed above, when inspecting the particle in the k-th field, whether or not the aperture position is shifted is determined by using the condition (the value V of the signal S9) obtained in the first field. With this determination, however, any condition in the first through (k−1)th fields may be employed. Alternatively, there may be used a condition in the field positioned one before the k-th field where the inspection is to be performed at all times, i.e., in the (k−1)th field.

Moreover, a determination to shift the aperture position is made when inspecting the k-th field. In this case, without taking trouble to obtain the optimum position while shifting the aperture position herein again, if the field having the same (or substantially approximate) as the pattern information (array) within, e.g., the k-th field is contained in the first through (k−1)th fields, this field is selected. The aperture position may be set by using the as-obtained condition (i.e., the optimum aperture position) in this selected field.

Further, the pattern information within the inspection range on the inspected object is stored beforehand in the memory. The relevant in-field pattern information is compared with the pattern information in the field position pone before it, i.e., the (k−1)th field in advance of inspecting the k-th field. Only when the array conditions (a pitch and a periodic direction, etc.) of the two are largely different, there may be made a comparison by use of the signal S9 transmitted from the photodetector 71 as shown in the embodiment discussed above. That is, the comparison is performed not per field but only when the in-field pattern information varies. Whether the aperture position is shifted or not may be thus determined.

Next, if the inspected object 19 of FIG. 12 is a reticle with a pellicle, when irradiated with the beam L9 or receiving the beam L15 from the inspected object 19, a support frame (hereinafter termed a pellicle frame) thereof, it can be also considered, gives a hindrance enough to make impossible an inspection of the reticle surface in the vicinity of the pellicle frame.

Even in such a case, in accordance with the embodiment of FIG. 12, the aperture of the annular-band light intercepting plate 63 is continuously rotatable through 180°. An angular range where both of the beam L18 and the beam L15 are not intercepted by the pellicle frame certainly exists in this 180° angular range. It is therefore possible to quickly inspect the particles on the entire surface of the reticle with the pellicle by employing the angular range where the beams are not intercepted by this pellicle frame.

Next, a seventh embodiment of the present invention will be explained with reference to FIGS. 14, 15, 16 and 17. In this embodiment, the present invention is applied to a case where the relative positions of the aperture and of the Fourier transform image of the inspected object are shifted on the pupil plane with variations in the incident vector of the beam on the inspected object. An explanation will be given by marking the same members as those of the particle inspecting apparatus in FIG. 12 with the like numerals.

Figure 14:
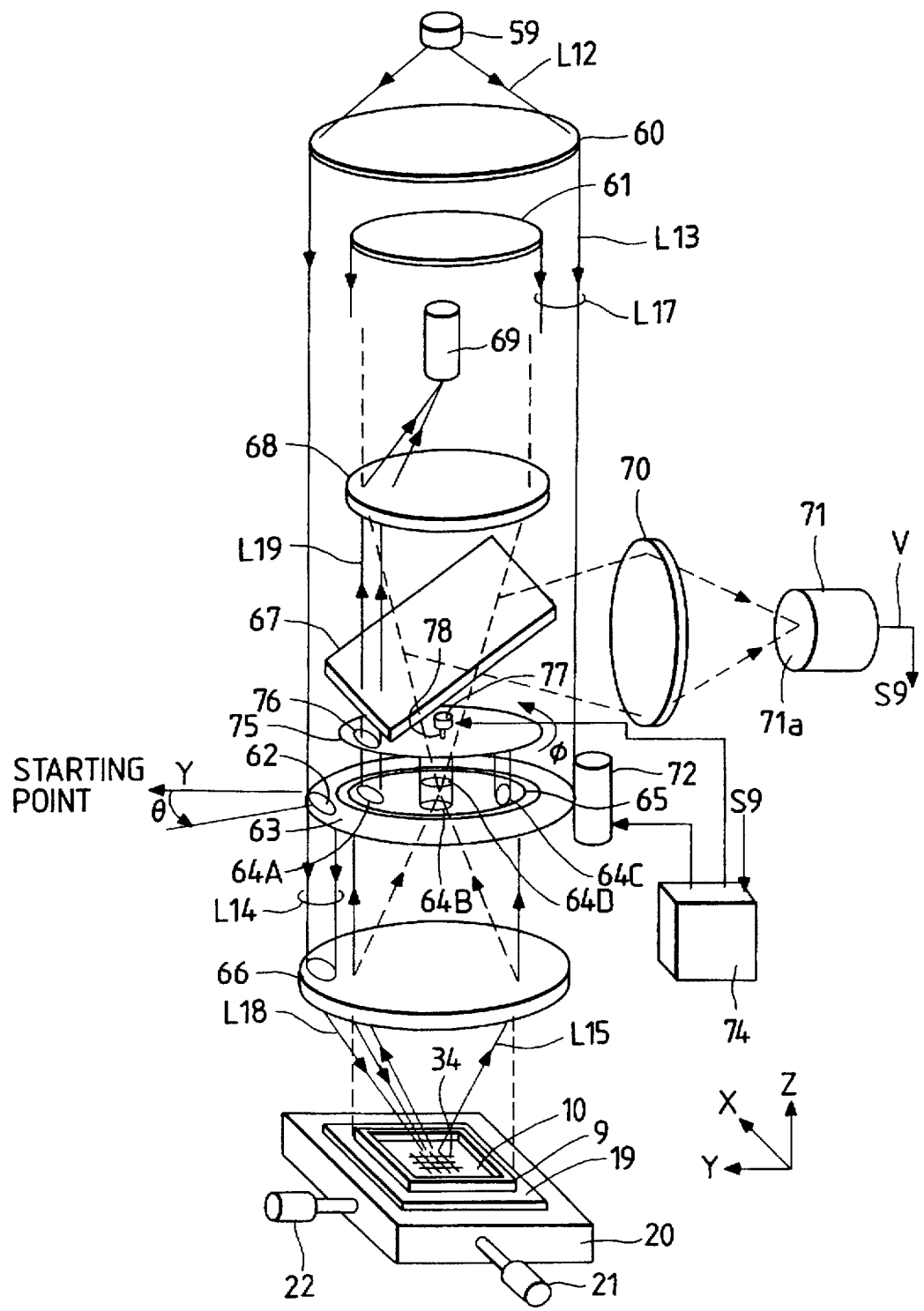
FIG. 14 is a perspective view illustrating a construction of the mechanism of the particle inspecting apparatus in a seventh embodiment of this invention.

FIG. 14 illustrates a geometry of the mechanism of the particle inspecting apparatus in this embodiment. Referring to FIG. 14, a reticle 19 is fitted with a pellicle 10 through a pellicle frame 9. Further, the original pattern 34 is formed on the reticle 4. The reticle 19 is placed on the stage 20. The stage 20 and the reticle 19 are movable in the X- and Y-directions by means of the driving units 21, 22. Moving quantities of the stage 20 in the X- and Y-directions are measured by an unillustrated length measuring unit (linear encoder, etc.). Further, the driving units 21, 22 are capable of rotating the stage 20.

A beam of light L12 emitted from a light source 59 is substantially collimated through a lens 60 into a beam of light L13. A circular light intercepting plate 61 is disposed in such a direction that the light source 59 and the light intercepting plate 61 are symmetrical with respect to the lens 60. A central part of the beam L13 outgoing from the lens 60 is intercepted by the light intercepting plate 61. A resultant beam of annular-band illumination light L17 falls on the annular-band light intercepting plate 63 formed with an aperture 62. A major diameter of the annular-band illumination light L17 is substantially equal to or slightly smaller than a major diameter of the annular-band light intercepting plate 63. A minor diameter of the annular-band illumination light L17 is substantially equal to or slightly larger than a minor diameter of the annular-band light intercepting plate 63. Further, the annular-band light intercepting plate 63 is so supported as to be rotatable in the peripheral direction, viz., in the θ-direction by means of the driving unit 72. A rotational angle thereof is also expressed by θ(0°≦θ≦360°). The rotational angle θ implies an angle made by the positive direction of the Y-axis and by the center of the aperture 62 of the annular-band light intercepting plate 63. The main control system 74 controls the operation of the driving unit 72. A beam of light L14 passing through the aperture 62 of the annular-band light intercepting plate 63 turns out a beam L18 through a light receiving lens 66 and is obliquely incident on the reticle 19.

On the other hand, beams of light L15 consist of diffracted light and scattered light generated from the particles such as dusts as well as from the pattern 34 on the reticle 19. The beams L15 passing through the light receiving lens 66 reach the light intercepting plate 65 provided on the pupil plane (i.e., the Fourier transform plane of the inspected surface of the reticle 19) of the light receiving lens 66. This is equivalent to such an arrangement that the light intercepting plate 65 is disposed on the Fourier transform plane, wherein f is the focal length of the light receiving lens 66, and following two distances are equally set to f, one distance extending from the reticle 19 to the principal point of the light receiving lens 66, another distance extending from the principal point of the light receiving lens 66 to the light intercepting plate 65. The light intercepting plate 65 includes four apertures 64A, 64B, 64C, 64D formed at in intervals of 90° with a starting point set in the positive direction of the Y-axis. In accordance with this embodiment, the light intercepting plate 65 is so disposed as to be substantially inscribed in the annular-band light intercepting plate 63.

Further, a light intercepting plate 75 formed with an aperture 76, a half-mirror 67, a lens and an imaging device composed of a two-dimensional charge coupled type imaging device (CCD) are arranged sequentially from the light intercepting plate 65 toward the circular light intercepting plate 61. A lens 70 and a photodetector 71 are arranged sequentially in such a direction that the light is reflected by the half-mirror 67. The light intercepting plate 75 among them is so disposed just behind the light intercepting plate 65 as to be substantially closely fit thereto. The light intercepting plate 75 is so supported as to be rotatable about a driving shaft 78 in a φ-direction, i.e., in the peripheral direction by means of a driving unit 77. The operation of the driving unit 77 is controlled by the main control system 74. The light intercepting plate 75 is rotated in the φ-direction, thereby making it possible to select a beam from an arbitrary one aperture among the four apertures 64A–64D of the light intercepting plate 65 via the aperture 76 of the light intercepting plate 75.

In the arrangement of, e.g., FIG. 14, the light intercepting plate 75 intercepts the beams passing through the three apertures 64B, 64C, 64D among the beams traveling through the four apertures 64A–64D of the light intercepting plate 65. However, only a beam L19 passing through the aperture 64A penetrates the aperture 76 formed in the light intercepting plate 75. In this case, the aperture 76 is so formed as to be equal to or larger than each of the four apertures 64A–64D. The beam L19 passing through the aperture 64A is not therefore intercepted by the aperture 76. Namely, the light intercepting plate 75 functions as a shutter means or a selecting means for selecting the beam passing through one of the four apertures 64A–64D. Accordingly, the driving unit 77, it may be enough, intermittently rotates the light intercepting plate 75 so that the aperture 76 comes to positions corresponding to the four apertures 64A–64D. The driving unit 77 is not required to rotate the continuously rotate the light intercepting plate 75.

Note that a liquid crystal shutter or the like capable of independently switching over the operation of transmitting and cutting off the beam may be provided in each of the apertures 64A–64D in stead of the light intercepting plate 75. Furthermore, in place of the fixed light intercepting plate 65, the rotatable light intercepting plate 75 itself is disposed, and a position of the aperture 76 of the light intercepting plate 75 may be fixed in any one of positions of the apertures 64A–64F according to the necessity.

The beam penetrating the half-mirror 67 in the light L19 passing through the aperture 76 of the light intercepting plate 75 is converged at the imaging surface of the imaging device 69 via the lens 68. The reticle 19 is conjugate to the imaging surface of the imaging device 69 with respect to the light receiving lens 66 and the lens 68. A conjugate image of the reticle 19 is formed on the imaging surface of the imaging device 69. However, an eyepiece may be disposed in place of the imaging device 69 so that the image of the reticle 19 is visually viewed.

On the other hand, the beam reflected by the half-mirror 67 in the light L19 passing through the aperture 76 of the light intercepting plate 75 is converged at the light receiving surface of the photodetector 71 via the lens 70. The light intercepting plate 65 provided on the pupil plane of the light receiving lens 66 is conjugate to the light receiving surface of the photodetector 71. The photodetector 71 photoelectrically converts the beams having a quantity substantially proportional to the beams traveling through the aperture 76 of the light intercepting plate 75. The photodetector 71 thereby outputs the detection signals B9. In this case, a light receiving surface 71a of the photodetector 71 serves as a pupil conjugate surface conjugate to all of the four apertures 64A–64D formed in the light intercepting plate 65. Consequently, the beam having a quantity proportional to the beam passing through arbitrary one of the apertures 64A–64D falls on the light receiving surface 71a of the photodetector 71. As a matter of course, there is selected only one of the four apertures 64A–64D, depending on the aperture 76 of the light intercepting plate 75f. Note that in this embodiment also, the main control system 74 processes the detection signal S9 and the imaging signal from the imaging device 69. The main control system 74 simultaneously generalize-controls the whole of other devices for controlling the respective driving units. Further, the imaging signal of the imaging device 69 may undergo the imaging process such as a filtering process and a differentiating process in this embodiment also.

Figure 15:
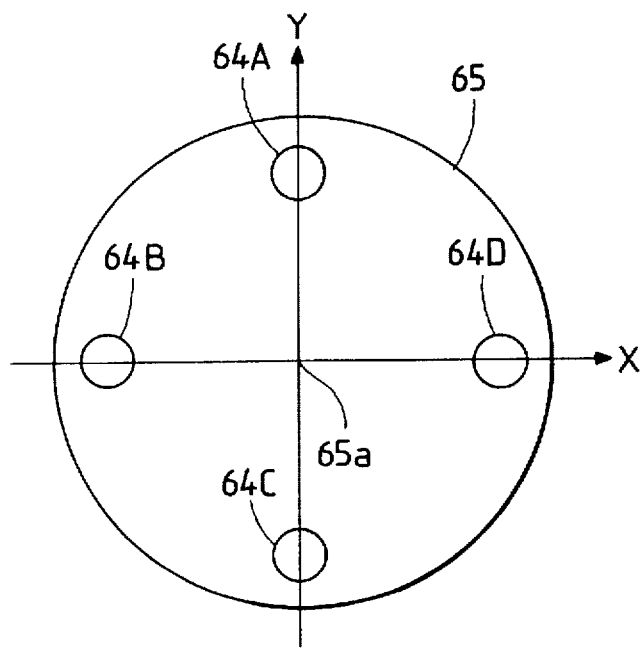
FIG. 15 is a plan view depicting a configuration of an aperture of a light intercepting plate 65 of FIG. 14.

A configuration of the light intercepting plate 65 will be explained in detail referring to FIG. 15. FIG. 15 is a plan view of the light intercepting plate 65 within a X-Y plane as viewed from the side of the light intercepting plate 75. The X- and Y-directions in FIG. 15 correspond directly to the X- and Y-directions in FIG. 14.

As depicted in FIG. 15, each of the four apertures 64A–64D in the light intercepting plate 65 assumes a circular shape but may take a square or a rectangle in accordance with this embodiment. Further, the four apertures 64A–64D all have the same minor diameter. Distances from a center 65a (coaxial with the optical axis of the light receiving lens 66 or the driving shaft 78) to centers of the respective apertures are all equal to each other.

Figure 16:
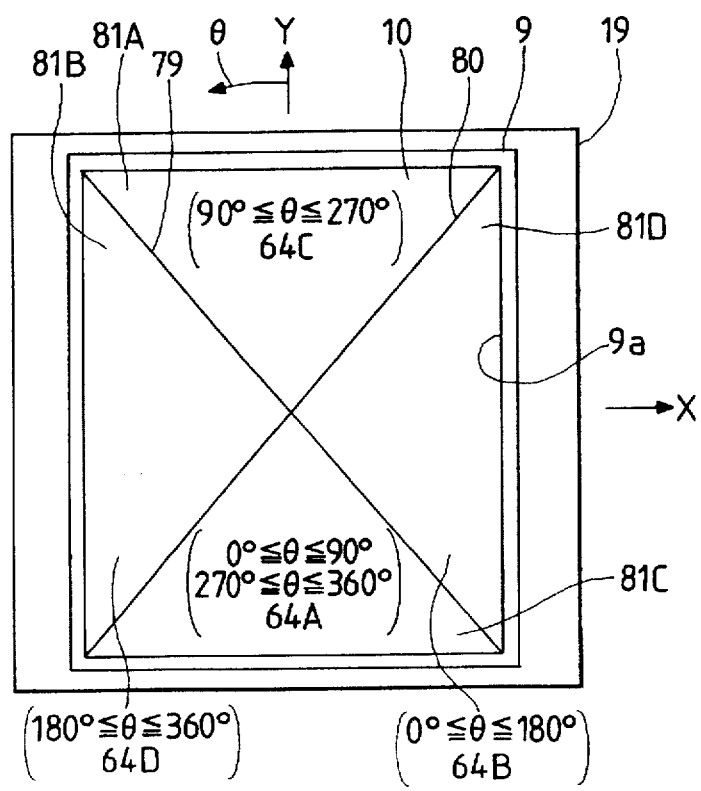
FIG. 16 is a plan view showing one example of a method of partitioning an inspection region of a reticle 19 of FIG. 14.

Next, one example of the particle inspection operation in this embodiment will be explained with reference to FIG. 16. FIG. 16 is a plan view of the reticle 19, of FIG. 14, fitted with the pellicle 10 through the pellicle frame 9 as viewed from the side of the light receiving lens 66. The X- and Y-directions in FIG. 16 correspond directly to the X- and Y-directions in FIG. 14. Further, an internal surface 9a of the pellicle-frame 9 assumes a rectangular shape in this embodiment. The internal surface of the pellicle frame 9 of the reticle 19 is partitioned into four inspection areas 81A–81D by using two diagonal lines 79, 80 which connects face-to-face vertexes of the internal surface 9a.

In this case, the beams L18 which are to obliquely be incident on the reticle 19 in the inspection areas thereof are not intercepted by the pellicle frame 9 but surely strike on the reticle 19. Hence, a continuously variable range of the rotational angle θ of the aperture 62 of the annular-band light intercepting plate 63 of FIG. 14 is defined such as 90°≦θ≦270° in a first inspection area 81A of FIG. 16. The range is 180°≦θ≦360° in a second inspection area 81B. The range is given by 0°≦θ≦90° plus 270°≦θ≦360° in a third inspection area 81C. The range is 0°≦θ≦180° in a fourth inspection area 81D. Further, the main control system 74 of FIG. 14 switches over the method of selecting an effective range of the rotational angle θ and any one of the four apertures 64A–64D on the basis of length measuring data of the unillustrated length measuring unit that correspond to the X- and Y-directional positions of the stage With this operation, the effective range of the rotational angle θ of the aperture 62 of the annular-band light intercepting plate 63 and one aperture selected from the four apertures 64A–64D are determined for each of the inspection areas 81A–81D of the reticle 19. In each of the inspection areas 81A–81D, the annular-band light intercepting plate 63 is rotated by actuating the driving unit 72 within the effective range of the rotational angle θ. A rotational angle $θ_0$ when the detection signal S9 of the photodetector 71 is minimized is thereby obtained.

The conjugate image of the reticle 19 is viewed through the imaging device 69, with the rotational angle θ of the aperture 62 of the annular-band light intercepting plate 63 being fixed to the rotational angle $\theta_0$. There is, as stated before, a comparatively small amount of diffracted light from the original pattern 34 of the reticle 19 with respect to the light passing through the aperture 76 of the light intercepting plate 75 at this rotational angle $\theta_0$. The imaging device 69 is therefore capable of clearly detecting (viewing) only the particles such as dusts on the reticle 19 in distinction from the pattern 34.

Figure 17:
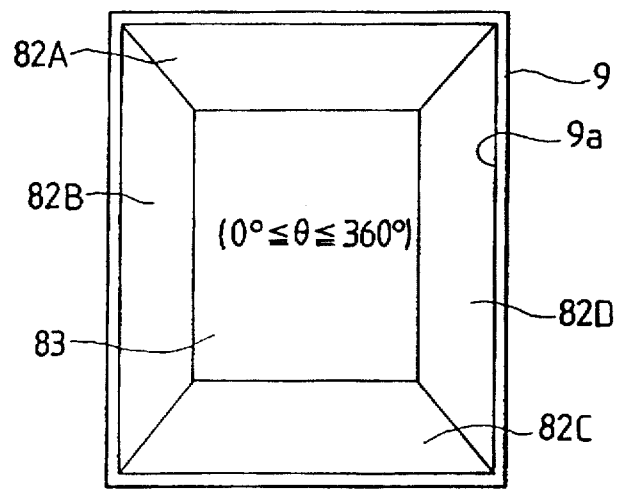
FIG. 17 is a plan view showing another method of partitioning the inspection region of the reticle 19 of FIG. 14.
Figure 18:
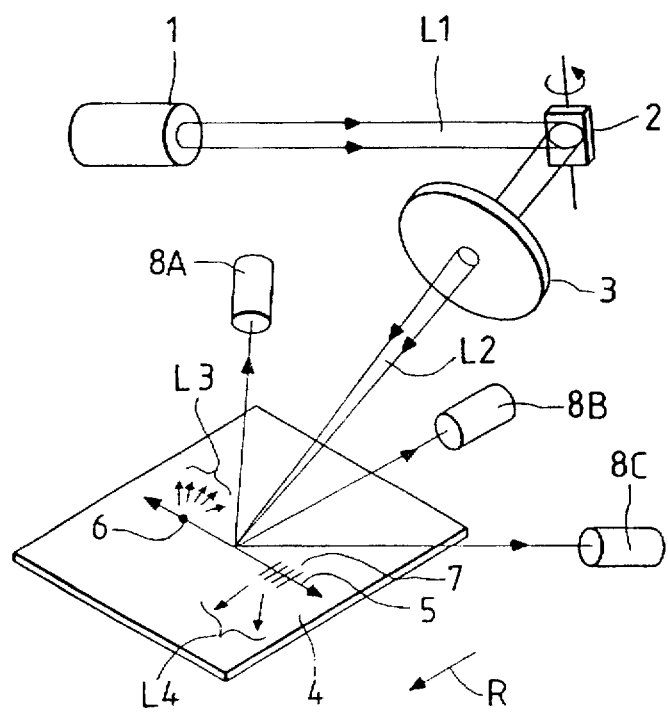
FIG. 18 is a perspective view illustrating a construction of a conventional particle inspecting apparatus.
Figure 19A:
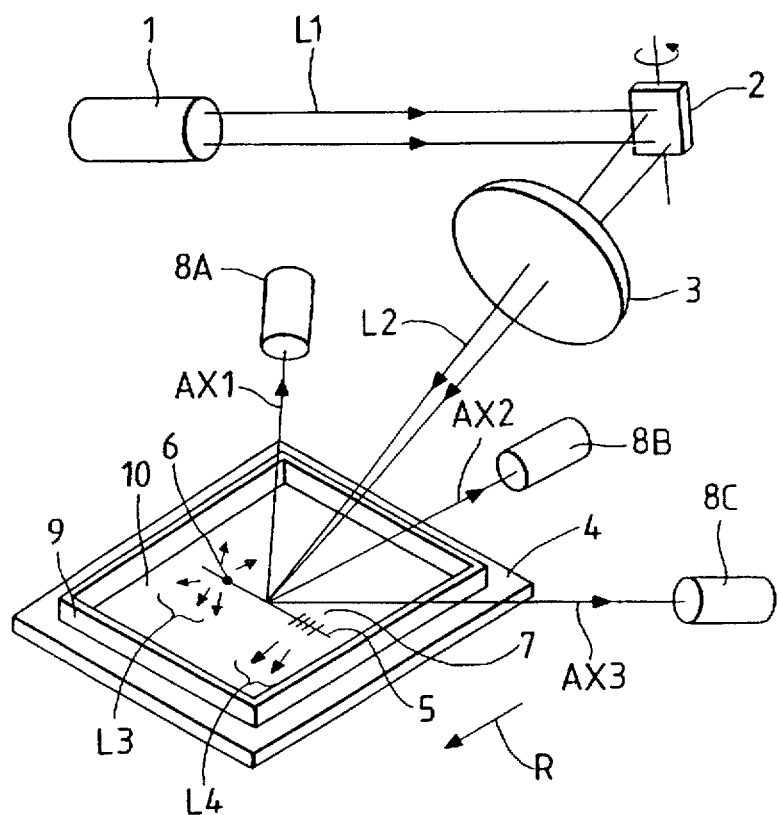
FIG. 19A is a perspective view illustrating a construction of the conventional particle inspecting apparatus capable of inspecting a reticle fitted with a pellicle.
Figure 19B:
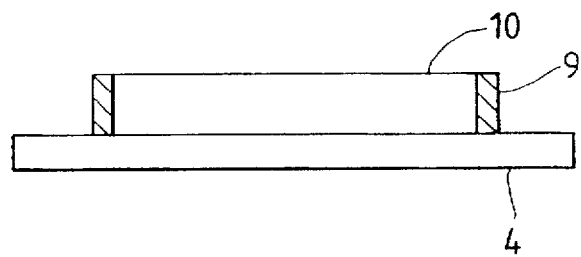
FIG. 19B is a sectional view illustrating the reticle with the pellicle.

Incidentally, the arrangement is not that the inspection region of the reticle 19 is partitioned into the four inspection areas as shown in FIG. 16 but that the inspection region surrounded with the internal surface 9a of the pellicle frame 9 on the reticle 4 may be partitioned into five inspection areas as illustrated in FIG. 17. In the example of FIG. 17, the fifth inspection area is provided at the central part of the 4-partitioned inspection areas of FIG. 16. The inspection region of the reticle 4 is partitioned into the four inspection areas 82A–82D in the peripheral part and one inspection area 83 at the central part. Then, a method of selecting the effective range of the rotational angle θ in each of the inspection areas 82A–82D and the aperture of the light intercepting plate 65 in FIG. 17 is the same as the method of selecting the effective range of the rotational angle θ in each of the inspection areas 81A–81D and the aperture in FIG. 16. The central inspection area 83 in FIG. 17 is, however, located apart from the pellicle frame 9. Consequently, the pellicle frame 9 does not intercept the beam L18 incident on the reticle 19 and the beam L15 from the reticle 19 at all. The effective range of the rotational angle θ of the aperture 62 of the annular-band light intercepting plate 63 can be therefore set such as $0° \leq \theta \leq 360°$ in the inspection area 83. A more optimal rotational angle $\theta_0$ can be therefore determined from a larger amount of optical information.

Further, if the pellicle frame 9 takes not the rectangular shape but a circular shape, it is possible to easily determine the method of selecting the effective range of the rotational angle θ of the aperture 62 of the annular-band light intercepting plate 63 and one of the four apertures 64A–64D. This involves the step of indicating where the beam L18 falls on the reticle 19 with polar coordinates.

Further, in this embodiment also, the rotational angle $\theta_0$ may be determined by use of the imaging signals from the imaging device 69, more specifically, by such an arrangement that a total sum (integral value of the output signals) of the signals per pixel of the imaging device is minimized.

Next, a variety of modified examples of the first to seventh embodiments discussed above will be explained.

(1) The optical axis of the light receiving lens 24 shown in FIGS. 5A, 8, 9A and 11 or of the light receiving lens 66 shown in FIGS. 12 and 14 is inclined to the inspected object 19. In this instance, it is feasible to receive the beams coming from the pattern 34 in a direction spatially more apart from the 0th-order diffracted light of the pattern 34 on the inspected object 19. Values of peaks 35A, 35B, 35C of the diffracted light shown in FIGS. 6A and 6B therefore decrease. There also decrease values of peaks 53A, 53B, . . . , 53I of the detection signal of FIG. 10 and values of the detection signal S9 of FIG. 14. A detection accuracy is thereby improved. This phenomenon is based on such an optical principle of diffraction that the quantity of diffracted light becomes smaller with a more separation from the 0th-order light.

(2) If the inspected object 19 is a glass substrate or metal mesh, etc. partially exhibiting a light transmitting property, the transmitting illumination can be attained.

(3) The inspected object 10 may be illuminated with the light having a single-wavelength or white light. However, the light having the single-wavelength is preferable in terms of making clear a brightness-difference of the Fourier transform image.

(4) Provided for the inspected object 19 are a plurality of optical systems (the light receiving lens 24 in FIGS. 5A, 9A and 11, the light receiving lens 24 in FIG. 8 and the light receiving lens 66 in FIGS. 12 and 14) in FIGS. 5A, 9A, 11, 8, 12 and 14. The optical information generated in a plurality of directions may be obtained from the inspected object 19. In this case, there is an advantage in which a greater amount of optical information can be obtained.

(5) In a step of exposing the reticle pattern on the wafer, a dust adhesion preventive film called a pellicle is coated over a pattern forming surface (or double surfaces) of the reticle through a rectangular frame (pellicle frame) in some cases. For detecting the dusts on the reticle surface of the reticle with the pellicle, the pellicle-coated reticle surface is irradiated with the beams. The optical information (scattered light or the like from the dusts) from this surface are thus detected. In this case, the pellicle frame becomes a hindrance sometimes, with the result that the reticle surface in the vicinity of the pellicle frame can not be inspected in some cases. Even in such a case, the apertures 25, 54 (in the embodiment of FIG. 11) are continuously rotatable through 180° in the embodiments of FIGS. 5A, 9A and 11. In the embodiment of FIG. 8, the aperture 44 is continuously rotatable 180°. In the embodiment of FIG. 12, the aperture 64 is continuously rotatable through 180°. Hence, a not-hindered-by-the-pellicle-frame angular range certainly exists within the 180° angular range. It is therefore possible to inspect the particles on the entire surface of the reticle with the pellicle by effecting the detection in this angular range.

(6) The photodetector 33 of FIG. 5, the photodetector 47 of FIG. 11 and the photodetector 71 of FIGS. 12 and 14 are employed with a view to measuring the quantities of beams penetrating the apertures 25, 45, 54, 64, 76, respectively. Accordingly, in the apparatuses of FIGS. 5A and 5B, the photodetector may be closely fixed to the rear surface of the light intercepting plate 26 (FIGS. 5A and 5B) just behind the aperture 25, thereby measuring the quantity of transmitted light via the aperture 25. Similarly, the photodetector may be closely fixed to the rear surface of the light intercepting plate 43 just behind the aperture 45 in the apparatus of FIG. 8 and to the rear surface of the light intercepting plate 55 just behind the aperture 54 in the apparatus of FIG. 11. The photodetector may also be closely fixed to the rear surface of the light intercepting plate 65 just behind the aperture 64 in the apparatus of FIG. 12 and to the rear surface of the light intercepting plate 76 just behind the aperture 76 in the apparatus of FIG. 14. The quantities of the transmitted light via the apertures (45, 54, 64, 76) can be thereby measured.

Besides, it is possible to shift the relative positions of the apertures (e.g., 25 and 45) and of the Fourier transform image of the pattern 34 on the inspected object 19 by rotating the inspected object 19 in any embodiment. Further, in accordance with any embodiment, the inspected object 19 may be illuminated vertically with the light; the transmitting illumination or fall-illumination may also be effected; and any illumination method, whether in a bright field or in a dark field, may be adopted. Additionally, there may be adopted such a system as to illuminate the inspected surface by one shot with the light in any embodiment. Furthermore, there may be combined the above-mentioned three methods (of moving the aperture, shifting the incident beam position and rotating the inspected object) in shifting the relative positions of the apertures (e.g., 25 and 45) and of the Fourier transform image of the pattern 34 on the inspected object 19 in order to enhance the capability of inspecting the particles in any embodiment.

Moreover, in accordance with the first to sixth embodiments also, a plurality of apertures may be formed within the Fourier transform plane P1. Then, time-division stops are provided in the plurality of apertures. The relative positions of the apertures and the Fourier transform image can be shifted by sequentially using the plurality of apertures without making the rotations and moving the stage as well. The signals as shown in FIGS. 6A-6C and 10 can be acquired.

Further, in each of the first through seventh embodiments, the photoelectric converting element such as a two-dimensional CCD array, etc. is provided on the Fourier transform plane (P1 of, e.g., FIG. 5A), and the detection signals are obtained sequentially on the unit of the predetermined area. With this arrangement also, the signals as shown in FIGS. 6A through 6C and 10 can be obtained. Besides, the signal processing explained in FIGS. 7A-7C may be conducted in each of the first through seventh embodiments.

Further, the relative positions of the apertures (25, 45, 54, 64, 76) and the Fourier transform image are determined to minimize the photoelectric signals S1, S6, S7, S8, S9 of the photodetectors 33, 47, 52, 71. In that instance, it follows that the spot of the Fourier transform image does not pass through the apertures (25, 45, 54, 64, 76), or if the spot passes therethrough, the spot light quantity of the Fourier transform image is small. The result is that a comparatively larger amount of optical information from the particles than from the Fourier transform image pass through the apertures (25, 45, 54, 64, 76). Only the particles can be detected by use of the beams passing through the apertures (25, 45, 54, 64, 76). For example, the relative positions of the apertures (25, 45, 54, 64, 76) and the Fourier transform image are determined to minimize the photoelectric signals S1, S6, S7, S8, S9. The photoelectric signals S1, S6, S7, S8, S9 are compared with predetermined threshold value, thereby enabling the detection of only the particles by employing the beams traveling through the apertures (25, 45, 54, 64, 76).

Further, in the apparatuses of FIGS. 5A, 5B and 8 (the first embodiment), the aperture position may be optimized (the operation to determine the relative positions of the apertures and the Fourier transform image so that the photoelectric signals S1, S6, S7, S8, S9 are minimized) in the sequence as shown in FIG. 13. More specifically, there is stored the value (minimum value of the photoelectric signal in the N-th inspection area) of the photoelectric signal under the optimum aperture condition obtained for the N-th inspection area (field). The value of the photoelectric signal when inspecting the (N+1)th inspection area is compared with the stored value of the photoelectric signal. If a difference therebetween falls within a predetermined allowable range, no optimization of the aperture position is effected (the aperture position is not shifted). Then, when inspecting the (N+1)th inspection area, the photodetectors 33, 47 photoelectrically converts the beams passing through the aperture position when inspecting the Nth inspection area. The photoelectric signals are compared with the predetermined threshold value, thereby making the particles detectable. Further, whether or not the aperture position is optimized at that time may be, as described above, judged based on the pattern information of the reticle.

Besides, in accordance with each of the first through seventh embodiments, the optical system (24, 32 of FIGS. 9A, 11 and 66, 88 of FIGS. 12, 14) for viewing the inspected surface 19 may be constructed to make its magnification variable high and low. In this case, the following applied example can be considered. The entire inspected surface 19 is inspected firstly at the low magnification. Thereafter, the stage 20 is moved to the coordinate position where the particle is detected, and the magnification is changed over to a high-powered level. Only portions in the vicinity of the area where the particle is detected are viewed.

Note that the aperture 62 of the annular-band light intercepting plate 63 is so configured as to be not only rotatable but also movable two-dimensionally within the plane parallel to the annular-band light intercepting plate 63 in the embodiments of FIGS. 12 and 14. The incident angle of the beam on the reticle 19 defined as an inspected object may be made variable. In this instance, an effective range of the incident angle of the beam is set corresponding to the respective inspection areas 81A-81D of the reticle 19 of, e.g., FIG. 16. Set subsequently are the effective range of the incident direction of the beam on the reticle 19, the effective range of the incident angle of the beam or the effective range of the position of the aperture selected in the light intercepting plate 65. This setting is done corresponding to the respective inspection areas 81A-81D of the reticle 19. Hereafter, the particles in the respective inspection areas 81A-81D of the reticle 19 are inspected well. For this purpose, the incident direction of the beam on the reticle 19, the incident angle of the beam or the position of the aperture selected in the light intercepting plate 65 may be set within the preset effective ranges in accordance with the inspection areas.

Eighth through eleventh embodiments of the present invention will hereinafter be described with reference to FIGS. 20 and 21. These embodiments will deal with a case where a relative position between an aperture and a Fourier transform image is varied on the pupil plane of the light receiving lens by changing a direction of an incident vector of the light with respect to the inspected object. The present invention is also, however, likewise applicable to a case where the direction of that incident vector is fixed, and the position of the aperture thereof is varied.

Figure 20:
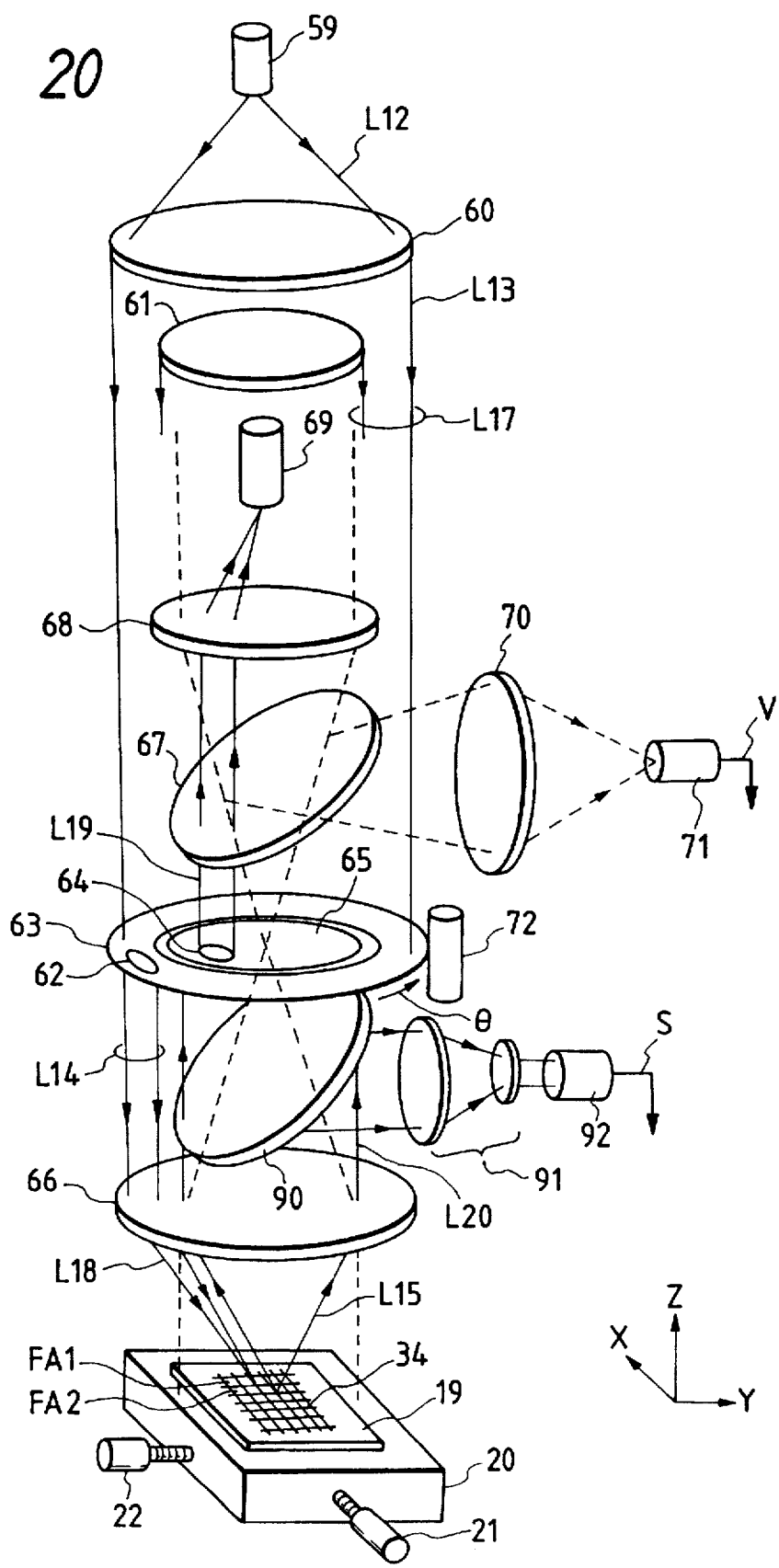
FIG. 20 is a perspective view illustrating a construction of a mechanism unit of the particle inspecting apparatus to which one embodiment of the particle inspecting method according to this invention is applied.

FIG. 20 shows one example of the particle inspecting apparatus to which the present embodiments are applied. Referring to FIG. 20, the same elements as those shown in FIG. 12 are marked with the like symbols, and their detailed explanations will be omitted. The stage 20 is moved in the X- and Y-directions through the driving units 21, 22. A field (viewing area) on the inspected object 19 existing on the stage 20 can be thereby moved.

A light source 59 is fixed above the inspected object 19, and a beam of light L12 emitted from the light source 59 are substantially collimated by a lens 60. However, a circular light intercepting plate 61 and the light source 59 are disposed in such a direction that the light intercepting plate 61 and the light source 59 are symmetric with respect to the lens 60. A central part of a beam of light L13 emerging from the lens 60 is intercepted by the light intercepting plate 61. The beam L13 turns out a beam of annular-band illumination light L17 and then falls on an annular-band light intercepting plate 63 formed with an aperture 62. A major diameter of the beam of annular-band illumination light L17 is slightly smaller than a major diameter of the annular-band light intercepting plate 63. A minor diameter of the beam of annular-band illumination light L17 is slightly larger than a minor diameter of the annular-band light intercepting plate 63. The annular-band light intercepting plate 63 is rotatably supported on a driving unit 72 in a θ-direction (its rotational angle is also expressed by θ) defined as a circumferential direction.

A light beam L14 passing through the aperture 62 of the annular-band light intercepting plate 63 becomes a light beam L18 through a light receiving lens 66 and obliquely falls on the inspected object 19. Beams of light L15 such as diffracted light, scattered light and the like that are generated from the inspected object 19 are converged by the light receiving lens 66. The converged light is incident on a circular light intercepting plate 65 disposed on the pupil plane (i.e., Fourier transform plane of the inspected object 19 through the light receiving lens 66). This is equivalent to placing the light intercepting plate 65 on the Fourier transform plane by such an arrangement that a distance from the inspected object 19 to a principal point of the light receiving lens 66 and a distance from the principal point of the light receiving lens 66 to the light intercepting plate 65 are equally set to f, where f is the focal distance of the light receiving lens 66.

For example, when inspecting particles in a certain narrow field (illumination area) FA1 on the inspected object 19, the stage 20 is moved to irradiate this field with a light beam L18. Thereafter, the annular-band light intercepting plate 63 is caused to make one rotation in the θ-direction and is fixed in such a position of the rotational angle θ that the detection signal V of the photodetector 71 is minimized. In this state, there exists no beam spot with a high-intensity Fourier transform image of a pattern 34 of the inspected object 19 in an aperture 64 of a light intercepting plate 65. Among the beams passing through aperture 64, a quantity of beam coming from the particles on the inspected object 19 is larger than that of the beam from the pattern 34. Accordingly, when viewing a conjugate image of the inspected object 19 by use of an imaging device 69, it is possible to clearly view the in-field particles on the inspected object 19.

In this case also, however, the quantity of beam from the pattern 34 is not 0. The particles are hard to view, and, therefore, the SN ratio may be enhanced by effecting imaging processes such as a filtering process and a differentiating process on the imaging signal of the imaging device 69. Only the particles on the inspected object 19 can be thereby displayed as, e.g., luminant points on the CRT display unit. The particles can be detected more efficiently.

Further, in the case of inspecting the particles on the entire surface of the inspected object 19, an inspection time gets long on the assumption that the optimal conditions are obtained by making one rotation of the annular-band light intercepting plate 63 in the θ-direction in respective fields FA1, FA2, . . . into which the entire surface thereof is finely partitioned. Under such circumstances, this embodiment takes the following steps of reducing the inspection time.

To start with, the apparatus is constructed such that a half-mirror 90 is provided between the light receiving lens 66 and the light intercepting plate 65; and a light beam L20 traveling through the light receiving lens 66 is split by the half-mirror 90. The beams reflected by the half-mirror 90 are reduced in parallel by a lens group 91 and incident on the imaging surface of the imaging device 92 constructed of a two-dimensional CCD or the like. The imaging surface of the imaging device 92 is disposed in a position optically equivalent to the light intercepting plate 65, i.e., disposed on the Fourier transform plane of the inspected object 19 through the light receiving lens 66. Hence, the imaging device 92 is capable of viewing a Fourier transform image of the pattern 34 from the inspected object 19 and a Fourier transform image of the scattered light from unillustrated particles. The imaging device 92 outputs an image signal S to an unillustrated signal processing unit.

Figure 21:
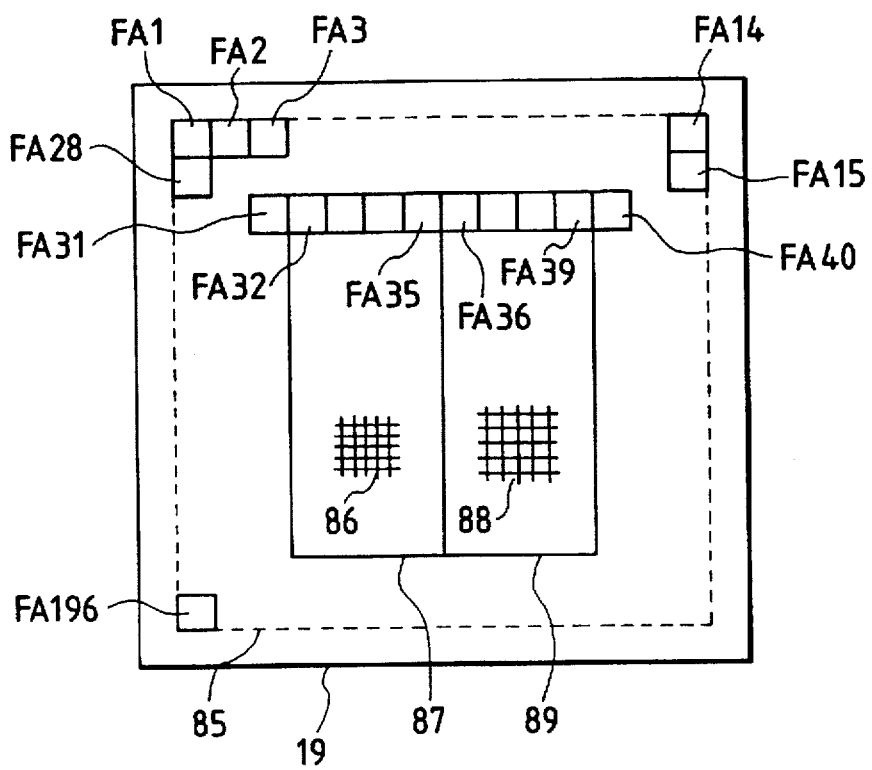
FIG. 21 is an enlarged plan view showing a method of partitioning the field on the surface of the inspected object 19 as a target for inspection in the embodiment.

Given next is a discussion on a variety of embodiments of inspecting the particles on the inspected object as show in FIG. 21 by use of the particle inspecting apparatus of FIG. 20.

FIG. 21 illustrates the surface of the inspected object 19 as a target of inspection. Referring to FIG. 21, the inspected object 19 is such a flat plate that its surface configuration is a square of, e.g., 80 mm×80 mm; and the particles are to be inspected in an inspection area of 70 mm×70 mm on the surface of the inspected object 19. Then, when a size of the field to be viewed by the particle inspecting apparatus of FIG. 20 is set to 5 mm×5 mm, it is required for inspecting the whole inspection area 85 of FIG. 21 that the inspection area 85 be partitioned into 196 fields FA1, FA2, . . . , FA196 and a field shift be effected 196 times. Further, a periodic pattern 86 with a fine pitch is formed in a rectangular area (hereinafter termed a [pattern area]) of 20 mm×50 mm in the inspection area 85. A periodic pattern 88 with a coarser pitch than the pattern 86 is formed in a pattern area 89 of 20 mm×50 mm adjacent to the pattern area 87. It is assumed that no pattern exists in areas other than the above within the inspection area 85.

In this case, in the inspection area 85, the 10 particle inspection starts from a first field FA1 at the left corner, and adjacent fields FA2, FA3, . . . are sequentially inspected. After reaching a field FA14 at the right end, the inspected object 19 is U-turned by driving the stage 20 of FIG. 20, and a 15th field FA15 just thereunder is inspected. Thereafter, the inspection is conducted from the field FA15 to the field FA28 at the left end in the left direction, and the inspected object 19 is T-turned. In this manner, bidirectional movements are made to inspect the fields within the inspection area 85, thus imaging the conjugate images of the respective fields FA1–FA196 by use of the imaging device 69 of FIG. 20; or alternatively, as described above, the visual observation is effected through the eyepiece. Next, the variety of embodiments of the specific inspecting method will be described.

[Eighth Embodiment]

The particle inspecting method in an eighth embodiment will be explained with reference to a flowchart of FIG. 22. First, in step 200 of FIG. 22, an irradiation area of a light beam L18 is set to the first field FA1 o the inspected object 19 by operating the driving units 21, 22 of FIG. 21. Then, in step 201, an image signal $S_1$ corresponding to a two-dimensional Fourier transform pattern outputted from the imaging device 92 is stored in a unillustrated memory. An image corresponding to this image signal $S_1$ is referred to as a first template. Hereinafter, an image corresponding to an image signal Si outputted from the imaging device 92 when viewing the i-th field FAi is termed an i-th template. The template in this embodiment is an item of image data for collating the Fourier transform image (two-dimensional image) picked up by the imaging device 91 with a Fourier transform image of other fields.

Next, in step 202, an aperture 64 of the annular-band light intercepting plate 6 is caused to make one rotation in the θ-direction by operating the driving unit 72 of FIG. 20 and thus fixed in an angular position of a rotational angle $\theta_1$ when the detection signal V of the photodetector 71 is minimized. Hereinafter, the operation of thus setting the angular position of the aperture 64 of the annular-band light intercepting plate 63 is called an [optimizing operation]. In this state, the imaging device 69 views a particle in the first field FA1 (step 203).

Thereafter, in step 204, the irradiation area of the light beam L18 is shifted to the second field FA2 on the inspected object 19 by driving the stage 20. An initial value of an integer i is set to 2, and the second field FA2 is generalized into the i-th field FAi (i=2 to 196). Then, the image signal Si obtained by the imaging device 92 imaging the Fourier transform pattern of the i-th field FAi is stored as the i-th template in the memory. In this case, the rotational angle of the annular-band light intercepting plate 63 remains set to the rotational angle $\theta_{i-1}$ used for viewing he (i–1)th field FA(i–1). In a state of being at this rotational angle $\theta_{i-1}$, in step 206, the (i–1)th template expressed by the image signal $S_{i-1}$ is compared with the i-th template expressed by the image signal Si of this time.

The template comparison in step 206 is a comparison between pieces of the two-dimensional image data. Specifically, there is determined whether or not the beam spot of the Fourier transform image of the diffracted light from the pattern on the inspected object 19 exists in the same position of the two-dimensional image. That is, it is because the coordinates of the beam spot of the diffracted light on the Fourier transform plane should be the same, if the pattern is the same. However, as will be discussed later in detail, when comparing pieces of two-dimensional image data with each other, though the attention is generally to be paid, there may be a deviation by approximately one pixel lengthwise and crosswise of the imaging surface of the imaging device 92. Then, when an allowable range is ±1–±2 pixels, and if conceived as the same two-dimensional image within this allowable range, it is determined that the positional data of the beam spot in the image signal $S_{i-1}$ of the Fourier transform image of the (i–1)th field is the same.

When determining the two templates are the same in step 206, the action shifts to step 207 without performing the optimizing operation, and the i-th field FAi is viewed by the imaging device 69. Whereas if the two templates are not identical with each other in step 206, the action moves to step 208, wherein there is effected again the optimizing operation of the rotational angle of the aperture 64 of the annular-band light intercepting plate 63. Thereafter, the action shifts to step 207 in which the i-th field FAi is viewed by the imaging device 69. The action shifts from step 207 to step 209, wherein there is determined whether or not the next field on the inspected object 19 is further inspected. That is, after adding 1 to a value of the variable number i, and, in step 210, whether or not the variable number i reaches an integer (N+1) is checked. The integer N indicates the number (196 in FIG. 21) of all the fields on the inspected object 19. Then, if the variable number i does not reach the integer (N+1) in step 210, the action shifts to step 204, wherein the particle in the next i-th field on the inspected object 19 is inspected. Then, the actions in steps 204 through 210 are repeated (N–1) times, and the second and subsequent fields FA2, FA3, . . . , FA196 on the inspected object 19 are inspected.

Specifically, in the case of the inspection area 85 of FIG. 21, the first optimizing operation of the aperture 64 of the annular-band light intercepting plate 63 is carried out in the first field FA1. Thereafter, there exists no pattern in all the fields up to the 31st field FA31, and, therefore, each field is viewed without performing the optimizing operation. Accordingly, the inspection time is reduced by an amount corresponding to an omission of the optimizing operation. Next, when moving to the 32nd field FA32, the field FA32 exists on the pattern area 87. Hence, the Fourier transform image of the diffracted light from the pattern 86 is viewed, and the 32nd template is created. This 32nd template is, however, obviously different from the template of the field FA31 in the previous field, and, therefore, the rational position of the annular-band light intercepting plate 63 is again conducted in the field FA32.

Similarly, when moving to the 36th field FA36 conceived as the first field of the pattern area 89 inclusive of the pattern 88 with a coarser pitch than the pattern 86, the template of the field FA36 is different from the template of the field FA35 posterior thereto, and therefore the optimizing operation is again carried out. The above actions are repeated up to the last field FA196, thus finishing the inspection of the particles on the inspected object 19. In accordance with this eighth embodiment, the 196 fields are inspected, and, therefore this requires the operation of creating the 196 templates and 31 repetitions of the optimizing operation.

[Ninth Embodiment]

In this ninth embodiment, the first template (hereinafter termed [template T1]) is created in the first field FA1 of FIG. 21, and, besides, the optimizing operation of the rotational position of the annular-band light intercepting plate 63 is performed. The unillustrated memory stores the rotational angle $\theta_1$ of the annular-band light intercepting plate 63 after the optimization has been effected. Next, when inspecting the second field FA2, the image signal S of the Fourier transform image of the field FA2 is comparatively collated with the template T1. However, the two are coincident with each other, and hence, the image signal S of the field FA2 is not stored as a template. Besides, the rotational position of the annular-band light intercepting plate 63 is not also conducted. That is, neither the creation of the templates nor the optimizing operation is performed from the second field FA2 to the 31st field FA31 of FIG. 21.

Next, in the field FA32, the image signal S of this field FA32 is apparently different form the template T1 and therefore stored as a second template T32 in the memory. Then, the optimizing operation of the rotational position of the annular-band light intercepting plate 28 is conducted, and, at the same time, a rotational angle $\theta_{32}$ of the annular-band light intercepting plate 28 is stored in the memory. Next, even when the image signal S of the 36th field FA36 is comparatively collated with two pieces of templates (templates T1, T32), they do not coincide with each other. Therefore, the image signal S of the field FA36 is stored as a third template T36 in the memory. Also, after performing the optimizing operation of the rotational position of the annular-band light intercepting plate 28, the set rotational angle $\theta_{36}$ is stored in the memory.

Thereafter, when the image signal S of the 40th field FA40 is comparatively collated with three templates (templates T1, T32, T36), the image signal S is coincident with the first template T1. Accordingly, instead of effecting the optimizing operation of the aperture 64 of the annular-band light intercepting plate 63, the rotational angle $\theta_1$ is called from the memory, and the rotational angle of the annular-band light intercepting plate 63 may simply be set to $\theta_1$. Similarly, all the image signals S of remaining fields are coincident with any one of the three templates T1, T32, T36. Hence, without affecting the optimizing operation, a value of the rotational angle $\theta$ of each of the fields coincident with the template is called from the memory, and the rotational angle of the annular-band light intercepting plate 28 may be set to this rotational angle θ.

In accordance with the ninth embodiment, with respect to the 196 fields of FIG. 21, it is enough to only store the data of the three templates and of three rotational angles θ and perform the three optimizing operations of the annular-band light intercepting plate 28. Accordingly, in comparison with the first embodiment, there are advantages in which the inspection time is reduced by an amount corresponding to a reduction in the number of times of the optimizing operation, and, at the same time, the storage capacity of the memory can be decreased by an amount corresponding to the reduction in the number of templates to be stored. Note that the storage capacity increases corresponding to a quantity of the data about the rotational angle θ, but the quantity of data about the rotational angle θ is meager as compared with a quantity of the data about one template. It is because the template entails the two-dimensional image data, while the rotational angle involves only one item of numerical data.

[Tenth Embodiment]

In accordance with this tenth embodiment, for instance, when inspecting the area formed with no pattern as in the fields FA1, FA2, . . . of FIG. 21, the diffracted light is not originally produced, and hence the memory stores, as a template $T_0$, a Fourier transform image when the pattern does not exist previously. The memory also stores, when an initial value of the rotational angle of the annular-band light intercepting plate 63 is set to $θ_0$, this initial value $θ_0$. With this operation, when the image signal S of the Fourier transform image of the first field FA1 is comparatively collated with the template $T_0$, the two are coincident with each other. Therefore, without performing the optimizing operation, the rotational angle θ of the annular-band light intercepting plate 63 is set to the initial value $θ_0$, and then the inspection takes place. The number of the optimizing operations can be thereby further reduced.

[Eleventh Embodiment]

In the tenth embodiment discussed above, when determining that the periodic pattern does not exist in a certain field composed of the image signal S of the imaging device 92 (i.e., when this image signal S is coincident with the template $T_0$), or when recognizing that the image signal S has no one- or two-dimensional periodicity in the eighth or ninth embodiment, the aperture 64 in the light intercepting plate 65 may be set anywhere because of undergoing no influence by the diffracted light from the pattern on the inspected object 19. Further, the aperture 64 may be eliminated.

Then, in this eleventh embodiment, in such a case, the annular-band light intercepting plates 63 and 65 of FIG. 21 are removed off the optical path. With this arrangement, a method of illuminating the inspected object 19 with the light entails an annular-band illumination for simply supplying the annular-band illumination light L17, while the image forming optical system becomes an image forming system having a numerical aperture corresponding to the major diameter of the light intercepting plate 65. A combination of this illumination method and the image forming optical system coincides with a vertical dark field-of-view illumination method in an ordinary optical microscope. At this time, an illumination light quantity is large corresponding to an aperture 64 in this eleventh embodiment. Further, the aperture 64 is not provided, and a light receiving quantity increases, correspondingly. It is therefore possible to view even a trace of particle enough to generate a trace of diffracted light. Moreover, a remarkable advantage is produced, wherein the numerical aperture increases, and, correspondingly, it is possible to view even an adjacent particle in separation (resolution). As a matter of course, even when removing the light intercepting plate 65 off the optical path, an aperture variable structure is adopted, and, if no pattern exists, a diameter of the aperture 64 in the light intercepting plate 65 may be increased.

Figure 1:
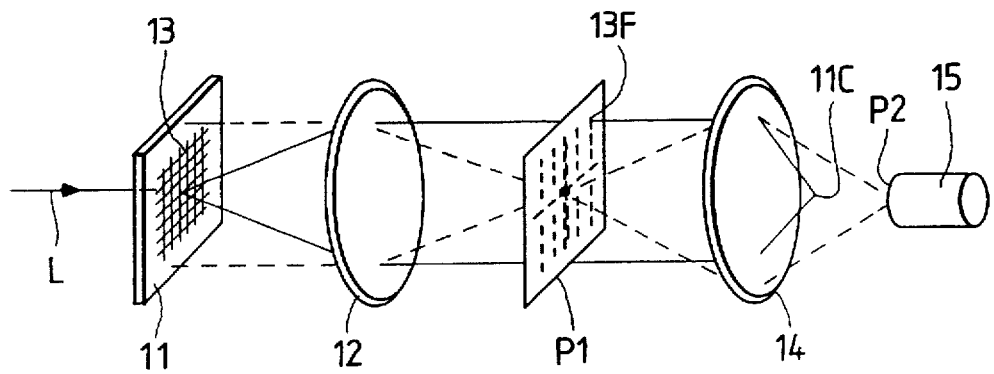
FIG. 1 is a perspective view of assistance in explaining the detection principle according to the present invention.
Figure 2:
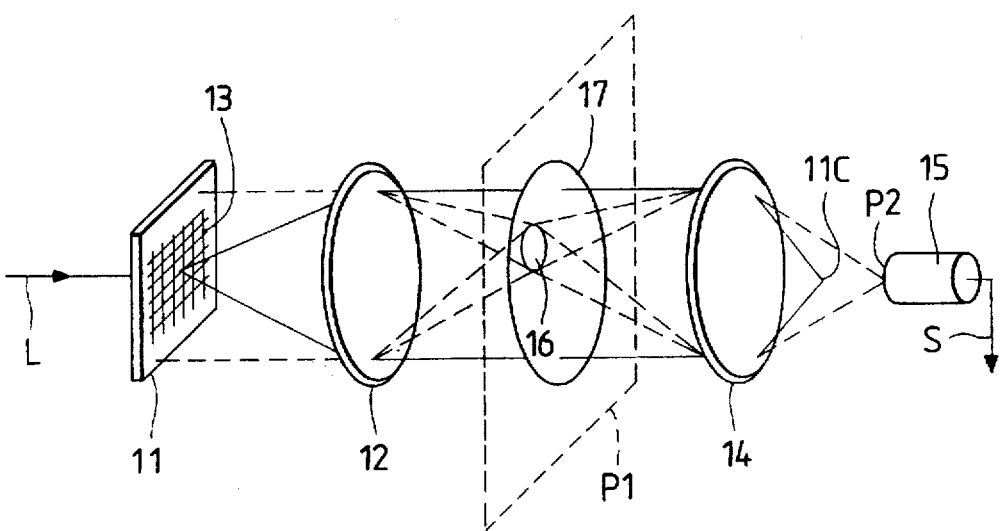
FIG. 2 is an explanatory perspective view of the detection principle of this invention but illustrates an arrangement wherein a light intercepting plate having an aperture is disposed on a pupil plane P1.
Figure 3A:
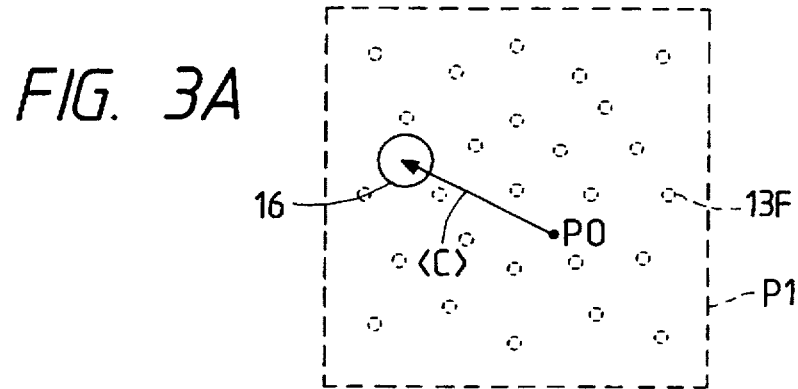
FIG. 3A is a front view showing a positional relationship between an aperture 16 and a Fourier transform image within the pupil plane P1.
Figure 3B:
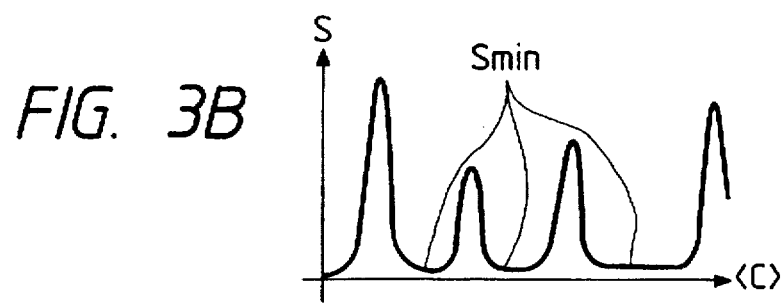
FIG. 3B is a waveform diagram showing one example where a photoelectric conversion signal S of a photodetector 15 of FIG. 2 changes when the positional relationship between the aperture 16 and the Fourier transform image 13F varies.
Figure 4:
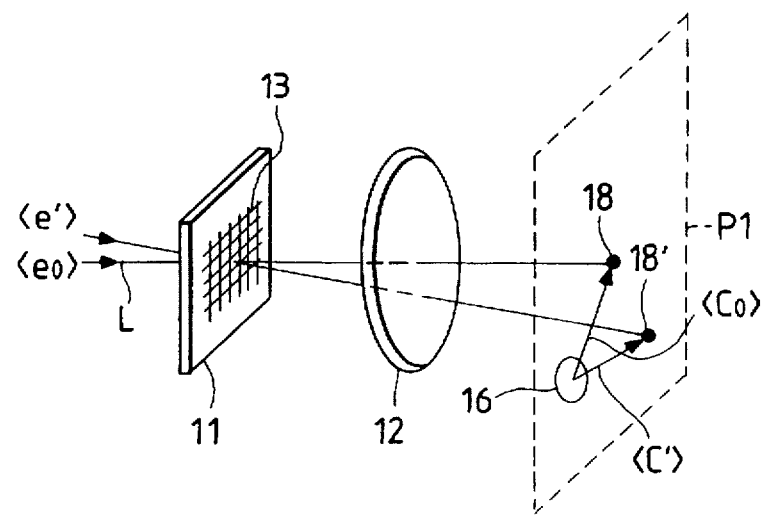
FIG. 4 is an explanatory view of the detection principle of this invention but illustrates an arrangement wherein the incident vector of the beam L upon the inspected surface changes.

Note that, in each of the embodiments discussed above, the diffracted light from the periodic pattern on the inspected object 19 is an aggregation of the beam spots as shown in FIG. 3A. Simply speaking, however, the template is like providing a black marking around only the beam spot as shown in FIG. 3A on the transparent sheet. This sheet is superposed on the respective beam spot patterns to see whether or not they are coincident with each other. This is the comparative collation. Whether they are coincident or not is determined based on whether a position and a pitch (period) of the beam spot on the sheet are coincident therewith or not. A trace of positional deviation on the whole does not present a problem.

Further, specifically, when the actual imaging device such as a two-dimensional CCD picks up the Fourier transform image, it may often happen that the Fourier transform image deviates by approximately one pixel on the whole on the imaging device due to influences of a slight deviation of the optical system of the mechanical system and also floor vibrations. Under such circumstances, it is required that the template permits such a positional deviation, and, therefore, the template is created on the assumption of forming a spot larger by one size than the beam spot of the actual Fourier transform image. That is, according to the previous example of the sheet, when marking the area of the beam spot in black, the marking is effected one size larger than the size of the actual beam spot. With this arrangement, even if the sheet (template) or the Fourier transform image deviates lengthwise and crosswise to some extent, there is caused no trouble in terms of the comparative collation.

Also, the template $T_0$ introduced in the tenth embodiment, speaking the previous example of the sheet, corresponds to the absolutely transparent sheet because of the optical data about the Fourier transform plane of the field in which the diffracted light is not produced at all. Note that, as a matter of fact, a positive reflected beam (0th-order diffracted light) of the illumination light reaches the Fourier transform plane, but, in the apparatus of FIG. 20, the aperture 62 for regulating the incident angle of the illumination light is formed outwardly of the light intercepting plate 65, with the result that the imaging device 92 does not receive the 0th-order diffracted light. If the some particles such as dusts or the like exist in the field formed with no pattern, however, a [hazy] Fourier transform image is obtained. It is recognized that this Fourier transform image is different from the template $T_0$, and the optimizing operation of the annular-band light intercepting plate 63 is performed in some cases.

Then, in this case, the attention is paid to that [hazy] Fourier transform image, and, when all the imaging pixels of the imaging device 92 sense beams of light assuming a given level (when each of the imaging signals of all the imaging pixels is a predetermined threshold value or greater), the comparative collation with the template $T_0$ is not carried out. Further, since the pattern does not exist in the field to be inspected, the viewing action is conducted as in the same way with the eleventh embodiment by removing the annular-band light intercepting plates 63 and 65 off the optical path without performing the optimizing operation of the annular-band light intercepting plate 63. The minute particles are thereby detected.

Given next is a description on a variety of examples of modification of the particle inspecting apparatus of FIG. 20 to which the above-described embodiments are applied.

Figure 22:
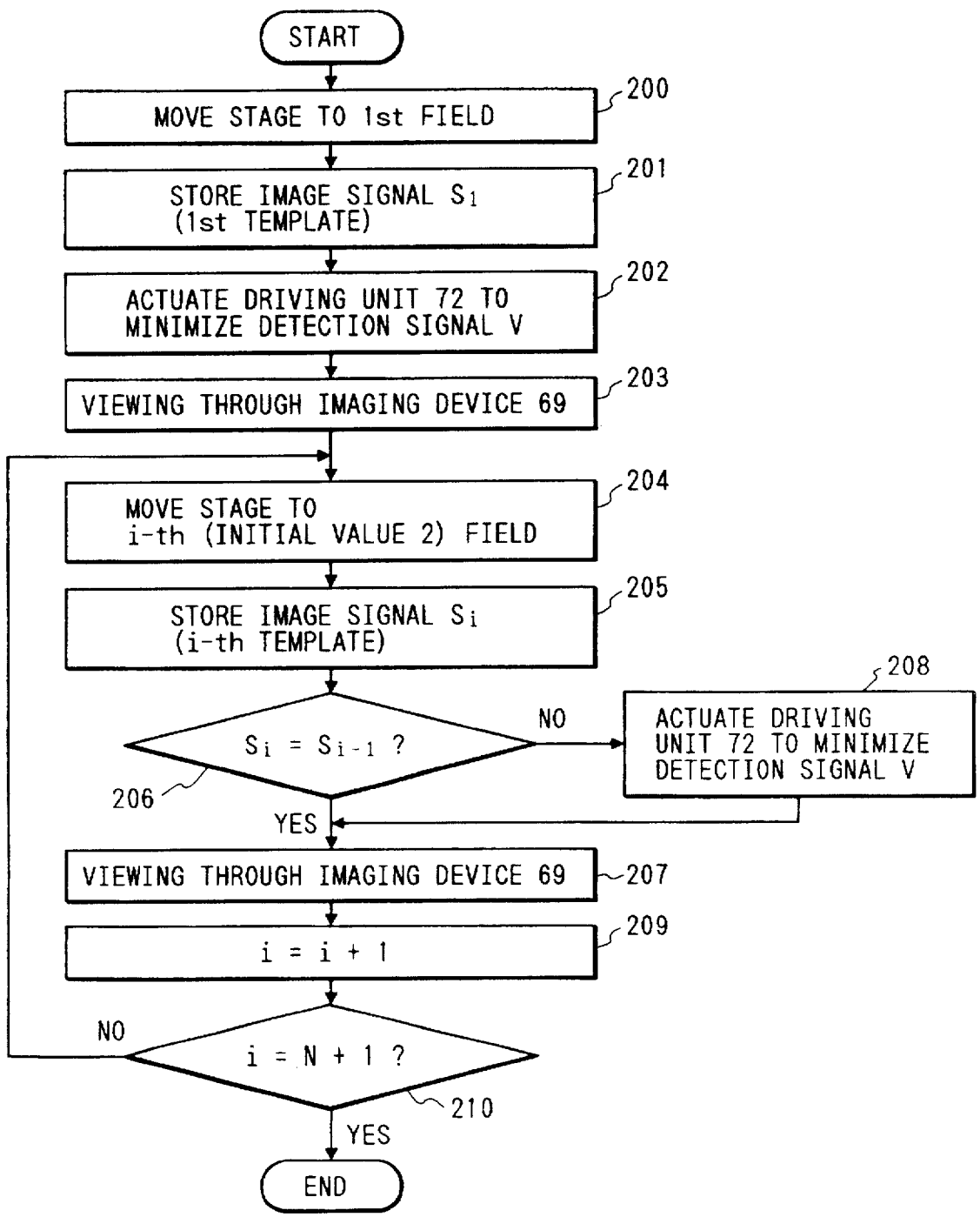
FIG. 22 is a flowchart showing the particle inspecting method in an eighth embodiment.

(1) The optical axis of the light receiving lens 66 of FIG. 22 is inclined to the inspected object 19. In this instance, the beams from the pattern 34 can be received in a direction spatially more part from the 0th-order diffracted light of the pattern 34 on the inspected object 19. Accordingly, the intensity of the Fourier transform image of the pattern 34 decreases, resulting in an improvement of the detecting accuracy. This phenomenon is based on such an optical principle of diffraction that the quantity of diffracted light becomes smaller with a more separation from the 0th-order light.

(2) If the inspected object 19 is a glass substrate or metal mesh, etc. partially exhibiting light transmitting property, the transmitting illumination can be attained.

(3) The inspected object 19 may be illuminated with the light having a single-wavelength or white light. However, the light having the single-wavelength is preferable in terms of making clear a brightness-difference of the Fourier transform image. As discussed above, the present invention is not limited to the above-discussed embodiments but can take a variety of configurations without departing from the scope of gist of the present invention.

In accordance with the eighth through eleventh embodiments, when there is a correlation between the Fourier transform pattern of the second field and the template of the first field, the aperture for inspection is set in the same relative positional relationship as that of the last time with respect to the Fourier transform pattern of the second field. Therefore, in the case of inspecting the particle on a similar pattern, it is possible to omit the optimizing operation of the relative positional relationship between the inspection aperture and the Fourier transform pattern. Accordingly, there are advantages wherein the particles can be detected without depending on the conditions of a density and a configuration of the original patterns of the inspected object, and, at the same time, the inspection time is short.

Further, if it can be considered that the Fourier transform pattern of the second field does not contain the periodic pattern (i.e., the pattern does not exist in the second field), the inspection time can be further reduced in the case of setting the inspection aperture in the same relative positional relationship as that of the last time with respect to the Fourier transform pattern of the second field.

If it can be also considered that the Fourier transform pattern of the second field contains no periodic pattern, the diameter of the inspection aperture is increased, and the particle in the second field is inspected from a conjugate image obtained by effecting an inverse Fourier transform on a large proportion of the Fourier transform pattern of the second field, thereby making it possible to detect the finer particle.

A twelfth embodiment of the particle inspecting apparatus according to the present invention will be explained with reference to FIGS. 23 and 24.

Figure 23:
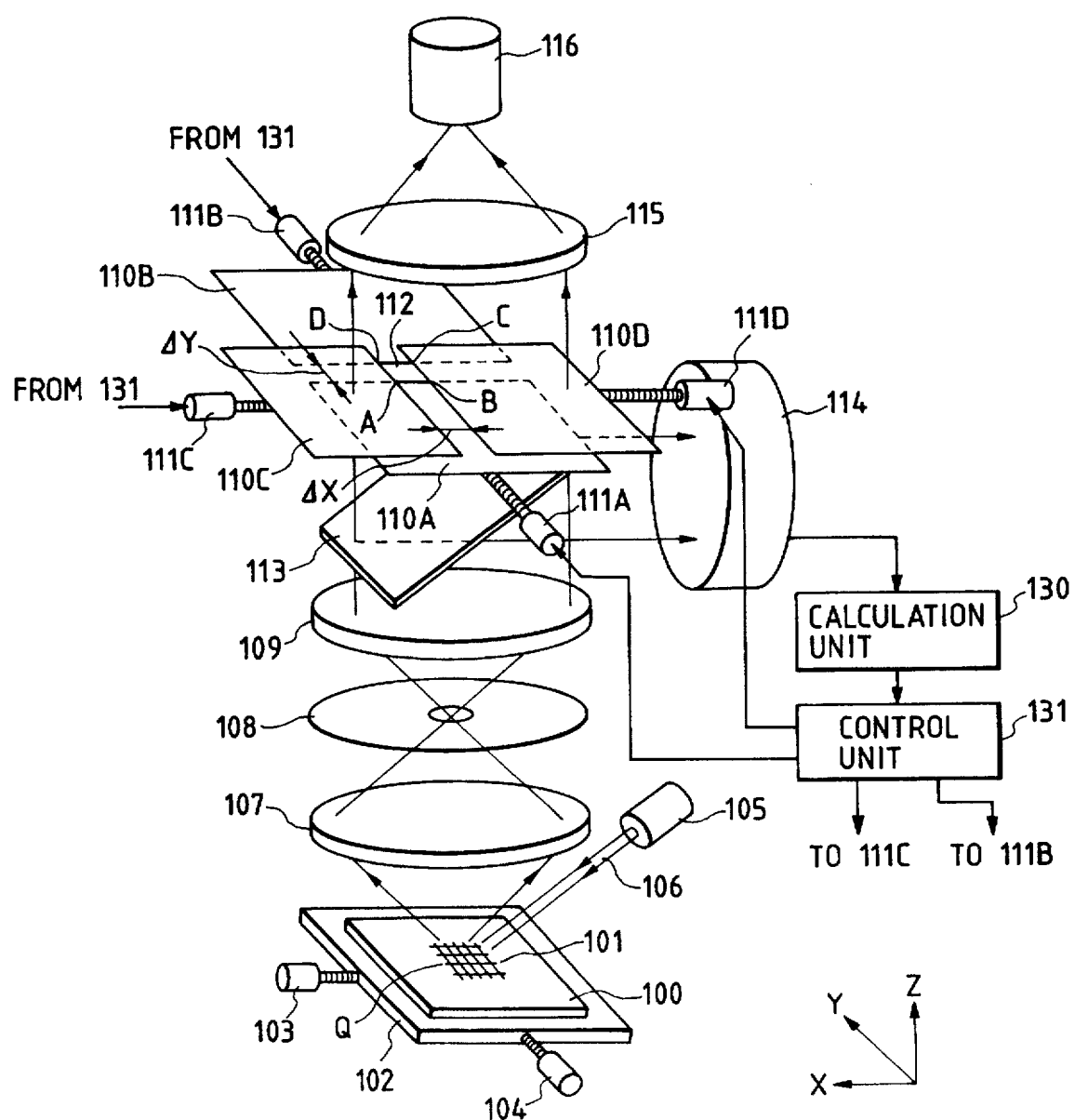
FIG. 23 is a perspective view illustrating a construction of the particle inspecting apparatus in a twelfth embodiment of this invention.

FIG. 23 illustrates a construction of the particle inspecting apparatus in this embodiment. Referring to FIG. 23, the surface of an inspected substrate 100 composed of a reticle or a wafer is formed with a pattern 101 such as a periodic circuit pattern. A particle on the pattern 101 or a dust adhered to the surface of the inspected substrate 100 is a target for inspection. The inspected substrate 100 is placed on an XY stage 102. The XY stage 102 is so constructed as to be movable in the X- and Y-directions respectively by driving units 103, 104, wherein a rectangular coordinate system of the plane parallel to the surface of the inspected substrate 100 is set as the X- and Y-axes.

A light beam 106 emitted from a light source 105 falls on a viewing field having a predetermined area surrounding a point Q on the surface of the inspected substrate 100. The diffracted light generated from the pattern 101 within the viewing field surrounding the point Q and the scattered light generated from a particle (unillustrated) within the viewing field are converged by a light receiving lens 107. Thereafter, the diffracted light and the scattered light pass through a field stop 108 provided on the plane conjugate to the surface of the inspected substrate 100. The diffracted light and the scattered light after unnecessary beams of light (outside the irradiation area of the light beam 106 or the viewing field) have been intercepted by the field stop 108 are further Fourier-transformed by a lens 109. Then, the Fourier transform pattern on the inspected substrate 100 is formed on the pupil plane (Fourier transform plane) of the lens 109.

Four pieces of light intercepting plates 110A, 110B, 110C, 110D are so disposed as to be movable on the pupil plane of the lens 109 or on the plane in the vicinity of the pupil plane. A beam of light of the Fourier transform pattern travels through a rectangular aperture 112 defined by the light intercepting plates 110A, 110B, 110C, 110D. In this case, the light intercepting plates 110A, 110B are independently movable in the Y-direction by driving units 111A, 111B, respectively. The light intercepting plates 110C, 110D are independently movable in the X-direction by driving units 111C, 111D. That is, the light intercepting plates 110A–110D are driven in translation by the driving units 111A–111D, thereby making it possible to set a position and a size of the rectangular aperture 112 substantially on the pupil plane to an arbitrary position and an arbitrary size, individually. A length of each of a pair of sides AB and CD in parallel to the X-axis is defined as $\Delta X$, and a length of each of a pair of sides BC and DA in parallel to the Y-axis is defined as $\Delta Y$, wherein A, B, C, D are respective apexes of this rectangular aperture 112.

A half-mirror 113 is provided between the lens 109 and the light intercepting plates 110A–110D. Beams of light reflected by the half-mirror 113 form a Fourier transform pattern on the surface of the inspected substrate 100. An imaging surface of imaging device (hereinafter called a [pupil plane imaging device]) 114 constructed of a two-dimensional CCD or the like for monitoring the Fourier transform image is disposed on this Fourier transform pattern forming plane. The imaging surface of the pupil plane imaging device 114 is provided in an optically equivalent position to the light intercepting plates 110A–110D, i.e., provided on the pupil plane (Fourier transform plane) of the lens 109. The imaging surface of the pupil plane imaging device 114 has a size enough to pick up an image having a size substantially equal to the pupil diameter of the lens 109, viz., all the images in a range equivalent to the X- and Y-directional range in which the rectangular aperture 112 is formed.

The pupil plane imaging device 114 supplies an arithmetic unit 130 with an imaging signal obtained by picking up the Fourier transform image on the surface of the inspected substrate 100. From that imaging signal, the arithmetic unit 130 obtains a position and a size of the aperture when, as will be stated later, the illuminance is minimized in that Fourier transform image. Items of data about the position and size of the aperture are supplied to a control unit 131. However, a predetermined lower limit is given to the size of that aperture. The control unit 131 drives the light intercepting plates 110A–110D in translation with the aid of the driving units 111A–111D, whereby the position and size of the aperture 112 are set to the position and size that are determined by the arithmetic unit 130.

Then, the beams of light passing through the rectangular aperture 112 are inverse-Fourier-transformed by a lens 115, thereby forming an image of the particle on the plane conjugate to the surface of the inspected substrate 100. An imaging plane of a viewing imaging device (hereinafter termed [an image plane imaging device]) composed of a two-dimensional CCD or the like is disposed on the plane conjugate to the surface of the inspected substrate 100. The image plane imaging device 116 picks up the image of the particle. Note that the particle image may be visually viewed by placing an eyepiece instead of the image surface imaging device 116.

Next, the operation of inspecting the particle on the surface of the inspected substrate 100 will be described. In this case, a periodic Fourier transform image 117 shown in FIG. 24 is formed on the imaging surface of the pupil plane imaging device 114 of FIG. 23. This Fourier transform image 117 is a Fourier transform pattern of the pattern 101 on the inspected substrate 100. The pupil plane imaging device 114 transforms the entire Fourier transform image 117 of FIG. 24 into an imaging signal.

The following is a description on a method of calculating a light quantity (illuminance) per unit area within the aperture 112 from the imaging signal of the pupil plane imaging device 114 by use of the arithmetic unit 130 and on an optimal control method of the size and the position of the aperture 112.

Figure 24:
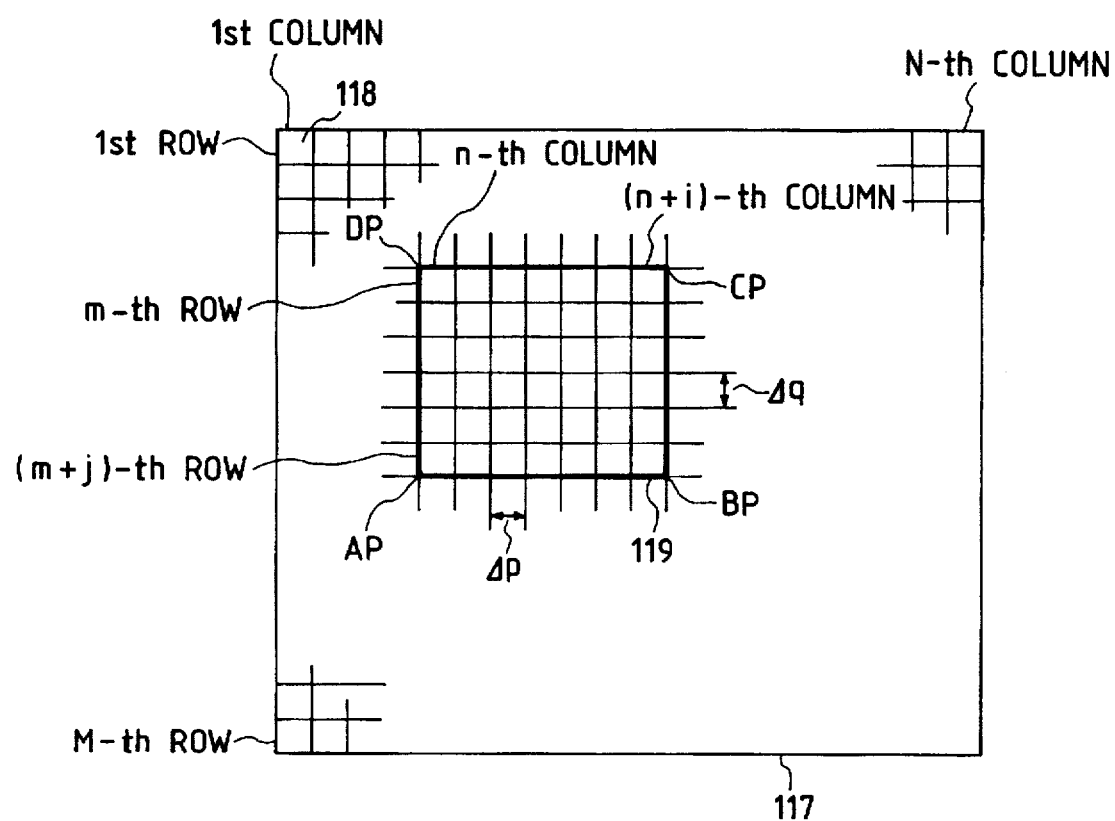
FIG. 24 is a diagram of assistance in explaining a method of processing an item of imaging data of an imaging device 114 in the twelfth embodiment.

FIG. 24 depicts a two-dimensional pixel configuration of the Fourier transform image 117 picked up by the pupil plane imaging device 114. Referring to FIG. 24, it is assumed that the Fourier transform image 117 consists of (M-th row×N-th column) pixels 118. Then, an item of light quantity data of a certain pixel existing in an arbitrary m-th row/n-th column position is expressed by I(m, n).

In this case, a position and a size of a rectangular pattern 119 composed of the pixels extending from the n-th column to an (n+i)-th column and from the m-th row to an (m+j)-th row are made corresponding to the position and the size of the rectangular aperture 112 of FIG. 23. Obtained subsequently is a light quantity per unit area within the pattern 119 depicted by a bold solid line. An integrated value $I_T$ of the light quantity in that pattern 119 is given by:

$$I_T = \Sigma_a \Sigma_b I(m+a, n+b)$$

where $\Sigma_a$ is the sum of 0 through j with respect to a suffix a, and $\Sigma_b$ is the sum of 0 through i with respect to a suffix b.

Hence, a light quantity f (i, j, m, n) per unit area within the pattern 119 is given as follows:

$$f(i,j,m,n) = I_T / \{(i+1)\Delta p \cdot (j+1)\Delta q\} \quad (1)$$
$$= \left\{ \Sigma_a \Sigma_b I(m+a, n+b) \right\} /$$
$$\{(i+1)\Delta p \cdot (j+1)\Delta q\}$$

where $\Delta p$ is the column-directional width of each pixel 118, and $\Delta q$ is the row-directional width.

The rectangular pattern 119, however, has to be a pattern solely existing in the Fourier transform image 117 surely including all the pixels, and, hence, the integers i, j, m, n larger than 0 in the formula (1) need to satisfy the following conditions:

$$(n+i) \leq N (2A)$$

$$(m+j) \leq M (2B)$$

As actual processing, the pupil plane imaging device 122 picks up the Fourier transform image obtained when irradiating the surface of the inspected substrate 100 with a light beam 106. This is stored as an item of two-dimensional pixel data in an (M-th row×N-th column) address of the storage unit (memory) within the arithmetic unit 130. Subsequently, under the conditions of the formulae (2A) and (2B), there are obtained values of the integers i, j, m, n when the light quantity f(i, j, m, n) per unit area in the formula (1) comes to a minimum value. However, lower limits α, β determined corresponding to the resolution of the particle to be detected are given to the integers i and j.

After determining the values of the integers i, j, m, n in this way, the control unit 131 of FIG. 23 drives the light intercepting plates 110A–110D in translation by use of the driving units 111A–111D, and the position and the size of the rectangular aperture 112 are set in a state corresponding to the values of the integers i, j, m, n.

Specifically, apexes AP, BP, CP, DP of the rectangular pattern 119 of FIG. 24 are made corresponding to the apexes A, B, C, D of the rectangular aperture 112 of FIG. 23. Set further, it is assumed, to 1:1 (equal magnification) are the size of the Fourier transform image on the placement plane of the light intercepting plates 110A–110D and the size of the Fourier transform image on the imaging surface of the pupil plane imaging device 1. At this time, the X-directional width ΔX and the Y-directional width ΔY of the rectangular aperture 112 are expressed such as;

$$\Delta X = (i+1) \cdot \Delta p \quad (3A)$$

$$\Delta Y = (j+1) \cdot \Delta q \quad (3B)$$

where Δp is the pitch of the pixel in a direction of the side AP-BP or the side CP-DP of the pattern 119 on the imaging surface of the pupil plane imaging device 114, and Δq is the pitch of the pixel in a direction of the side BP-CP or the side DP-AP.

Besides, the light intercepting plates 110A–110D are moved by the driving units 111A–111D to form the rectangular aperture 112 in a position shifted by n·Δp in the X-direction and m·Δq in the Y-direction from the position on the placement plane of the intercepting plates 110A–110D of FIG. 23, which position corresponds to the 1st-row/1st-column pixel of FIG. 24.

In this state, the image plane imaging device 116 supplies an unillustrated TV monitor with the imaging signals to provide a display on a monitor screen. When viewing on the monitor screen or the above-mentioned visual viewing through the eyepiece is conducted, it is possible to inspect only the particles by eliminating the diffracted light from the pattern 101 on the inspected substrate 100.

Next, another processing method entails selecting the width ΔX and ΔY which indicate a size of the rectangular aperture 112 of FIG. 23 from, e.g., three sets of combinations such as $(\Delta X_1, \Delta Y_1)$, $(\Delta X_2, \Delta Y_2)$, $(\Delta X_3, \Delta Y_3)$. For this purpose, according to the configuration of FIG. 23, the control sequence of the driving units 111A–111D may be restricted to set the size of the aperture 112 to any one of the three sets of combinations of the size. Alternatively, three types of rectangular apertures are prepared beforehand, and a switchable or exchangeable construction may be provided.

In this case, it follows that the consideration about integers i, j showing a size of the pattern 119 on the pupil plane imaging device 114 of FIG. 24 may be given to only three sets of combinations such as $(i_1, j_1)$, $(i_2, j_2)$, $(i_3, j_3)$, corresponding to the aperture sizes of $(\Delta X_1, \Delta Y_1)$, $(\Delta X_2, \Delta Y_2)$, (ΔX$_3$, ΔY$_3$). However, (ΔX$_k$, ΔY$_k$) and (i$_k$, j$_k$) are related such as: ΔX$_k$=(i$_k$+1)·Δp, ΔY$_k$=(j$_k$+1)·Δq, (k=1 to 3). Under this condition, when obtaining a combination of the integers in the case of taking the minimum value in the formula (1) and values of the integers m, n, the time necessary for calculating the position and the size of the rectangular aperture 112 can be reduced.

Figure 25:
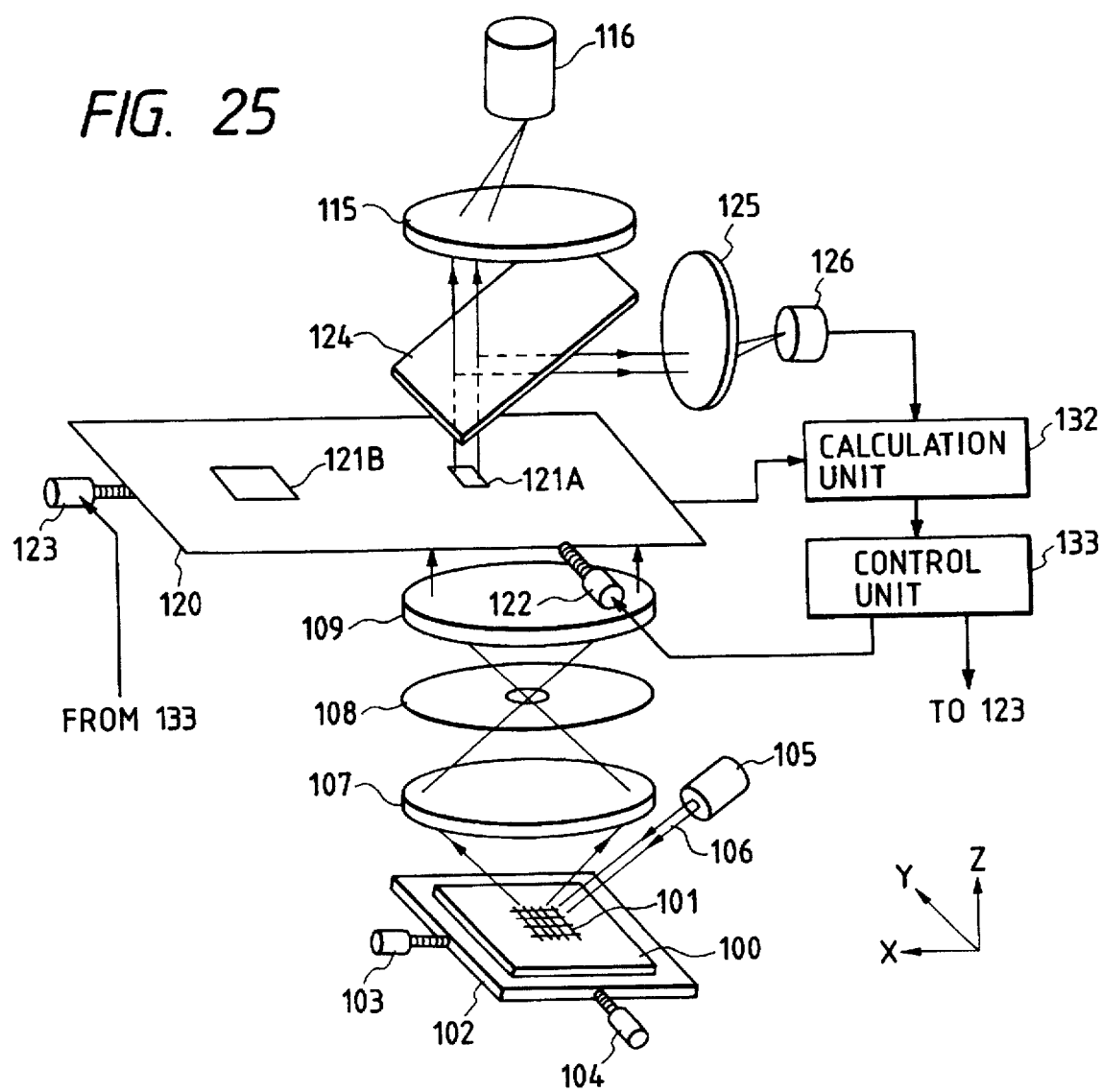
FIG. 25 is a perspective view depicting a construction of a thirteenth embodiment of the present invention.

Next, a thirteenth embodiment of the present invention will be described with reference to FIG. 25. Referring to FIG. 25, the same members as those in FIG. 23 are marked with the like symbols, and their detailed explanations will be omitted. Referring again to FIG. 25, a light intercepting plate 120 is formed with a plurality (two types in FIG. 25) of rectangular (circular shape is also available) apertures 121A, 121B each having a different size. This light intercepting plate 120 is disposed on a Fourier transform plane through the lens 109 with respect to the surface of the inspected substrate 100 or a plane in the vicinity of this Fourier transform plane. The light intercepting plate 120 is so supported as to be drivable in the Y- and X-directions respectively by driving units 122, 123. Further, the driving unit 123 also serves to perform an operation to switch (set the plate on and off the optical path) the rectangular apertures 121A, 121B.

Further, a half-mirror 124 is provided between the light intercepting plate 120 and a lens 115. Beams of light reflected by the half-mirror 124 are condensed at a light receiving surface of a photoelectric detector 126 by a condenser lens 125. The photoelectric detector 126 involves the use of a silicon diode, a photo multiplier and the like. The photoelectric detector 126 photoelectrically converts a light quantity proportional to a quantity of light passing through the rectangular aperture 121A or 121B (aperture 121A in the state of FIG. 25). A photoelectric signal of the photoelectric detector 126 is supplied to an arithmetic unit 132. Supplied also from the light intercepting plate 120 to the arithmetic unit 132 is an item of data about the aperture 121A or 121B which is presently set on the Fourier transform pattern. The arithmetic unit 132 calculates an illuminance of the light traveling through the aperture 121A or 121B and supplies the calculated illuminance to a control unit 133. The control unit 133 locates the light intercepting plate 120 to minimize the illuminance of the light beam passing through the aperture 121A or 121B with the aid of the driving units 122, 123. Other configurations are the same as those in FIG. 23.

The operation of inspecting the particles on the surface of the inspected substrate 100 will be explained with reference to FIG. 25. First, in a state where the rectangular aperture 121A enters the light beam (Fourier transform pattern) passing through the lens 109, the light intercepting plate 120 is moved in the X- and Y-directions substantially on the pupil plane by use of the driving units 122, 123. Obtained are X- and Y-coordinates of the light intercepting plate 120 when the photoelectric signal (proportional to the quantity of received light) of the photoelectric detector 126 is minimized. A storage unit such as a memory in the control unit 133 stores the X- and Y-coordinates and an item of data about the light quantity per unit area at that time. Subsequently, the light intercepting plate 120 is largely moved by the driving unit 123 so that the rectangular 121B enters the Fourier transform pattern. Thereafter, absolutely the same operations as those in the case of the aperture 121A are repeated, and the data are stored in the storage unit incorporated into the control unit 133.

Supposing that an area ratio of the aperture 121A to the aperture 121B is 1:4, the arithmetic unit 132 obtains, as the light quantity data per unit area, a value given by dividing the photoelectric signal of the photoelectric detector 126 in the case of the aperture 121A and the photoelectric signal of the photoelectric detector 126 in the case of the aperture 121B by a coefficient of the ratio 1:4. Accordingly, the arithmetic unit 132 determines which aperture of the apertures 121A and 121B to transmit a less quantity of light per unit area. The position of the light intercepting plate 120 is set to effect the switchover to the aperture exhibiting a lower illuminance by use of the data (i.e., the X- and Y-coordinates of the light intercepting plate 120) of the lower illuminance.

Figure 26:
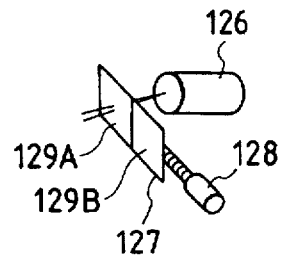
FIG. 26 is a perspective view illustrating the principal portion in an example of modification of the thirteenth embodiment.

Note that a transmission factor of a filter plate 127 disposed in front of the photoelectric detector 126 may be switched by using a driving unit 128 as illustrated in FIG. 26, interlocking with the switching operation of, e.g., the rectangular apertures 121A, 121B instead of dividing the respective photoelectric signals of the photoelectric detector 126 by the coefficient determined by the aperture area ratio. That is, the filter plate 127 is constructed by combining glass plates 129A, 129B having transmission factors different from each other. When the area ratio of the rectangular aperture 121A to the aperture 121B is 1:4, the transmission factors of the glass plates 129A, 129B are set to 100% and 25%, respectively. Then, when the aperture 121A enters the optical path, the glass plate 129A is disposed immediately in front of the photoelectric detector 126. When the aperture 121B enters the optical path, the glass plate 129B comes just before the photoelectric detector 126. With this arrangement, the photoelectric signal of the photoelectric detector 126 represents the aperture transmitting light quantity per unit area as it is when using any one of the apertures 121A, 121B, and, hence, it follows that a simple numerical comparison may suffice.

Developing further this embodiment, it can be appreciated that glass plates (filter) having the same transmission factors as those of the glass plates 129A, 129B of FIG. 26 are bonded directly to the respective rectangular apertures 121A, 121B of FIG. 25; that is, the quantity of light passing through the larger aperture is reduced corresponding to its area by the filter having a lower transmission factor, and the light may be received by the photoelectric detector 126. In this case, the arithmetic unit 132 of FIG. 25 may be omitted.

As described above, the present invention is not limited to the embodiment given above but can take a variety of configurations without departing from the scope of the gist of the present invention.

As described above, in accordance with the twelfth and thirteenth embodiments, the size and the position of the aperture for eliminating the beam spot of the original periodic pattern from the Fourier transform pattern are optimized according to the measured result of the illuminance measuring unit for measuring the illuminance of the light beam passing through the aperture. Accordingly, there is such an advantage that only the particles can be detected without depending on the conditions such as the density and the configuration of the original pattern of the inspected object.

Further, this illuminance measuring unit includes the imaging device for imaging the Fourier transform pattern and the arithmetic unit for calculating the illuminance of the light beams passing through the aperture by image-processing the imaging signal from the imaging device. In this case, a small number of mechanical operations are performed, and, therefore, the optimization of the aperture can be conducted at a high speed.

On the other hand, the illumination measuring unit includes the photoelectric converting unit for photoelectrically converting the light beam passing through that aperture and the arithmetic unit for obtaining the illuminance of the light beam passing through the aperture on the basis of the aperture area and the photoelectric conversion signal from the photoelectric converting unit. In this case, the actual illuminance can be accurately measured.

Note that this invention is not restricted to the embodiments discussed above but may, as a matter of course, take a variety of working modes without deviating from the spirit and scope of the invention.

What is claimed is:

1. A method of inspecting particles on an object to be inspected from optical data obtained by irradiating the inspected object with beams of light for inspection and converging light beams from the inspected object, said method comprising:
a first step of obtaining a first Fourier transform pattern by Fourier-transforming the beam from a first field on the inspected object, storing the first Fourier transform pattern as a two-dimensional template, forming a conjugate image of the first field by effecting an inverse Fourier transform on a component within an inspection aperture which is set in a predetermined relative positional relationship with respect to the first Fourier transform pattern and thus inspecting the particle in the first field by use of the conjugate image; and a second step of obtaining a second Fourier transform pattern by Fourier-transforming the beam from a second field different from the first field on the inspected object, forming a conjugate image of the second field by effecting the inverse Fourier transform on the component within the inspection aperture which is set in the predetermined positional relationship with respect to the second Fourier transform pattern and thus inspecting the particle in the second field by use of the conjugate image, wherein said first step involves setting a relative positional relationship between the first Fourier transform pattern and the inspection aperture to minimize a quantity of light passing through the inspection aperture, and wherein said second step involves setting, if there is a correlation between the second Fourier transform pattern and the template, the inspection aperture in the same relative positional relationship as that in said first step with respect to the second Fourier transform pattern but setting, if there is no correlation between the second Fourier transform pattern and the template, a relative positional relationship between the second Fourier transform pattern and the inspection aperture to minimize the quantity of light passing through the inspection aperture.

2. The method according to claim 1, wherein said second step involves, if it can be considered that the second Fourier transform pattern contains no periodic pattern, setting the inspection aperture in the same relative positional relationship as that in said first step with respect to the second Fourier transform pattern.

3. The method according to claim 1, wherein said second step involves, if it can be considered that the second Fourier transform pattern contains no periodic pattern, inspecting the particle in the second field by use of the conjugate image obtained by effecting the inverse Fourier transform on a large proportion of components of the second Fourier transform pattern by increasing a diameter of the inspection aperture.

4. An apparatus, having a light irradiating device for irradiating an object to be inspected with beams of light for inspection and a light converging device for converging beams of light from the inspected object, for inspecting particles on the inspected object by use of the converged beams of light, said apparatus comprising:
a first transform optical system for Fourier-transforming the light beams from the inspected object;

an aperture setting device for setting an aperture having a variable relative positional relationship with the Fourier transform pattern of the inspected object and a variable area on a Fourier transform plane of the inspected object through said first transform optical system;

an illuminance measuring device for obtaining a light quantity, per unit area, of light beams passing through the aperture;

a control device for setting the relative positional relationship between the aperture and the Fourier transform pattern and also the area of the aperture through said aperture setting device to minimize the light quantity, per unit area, of the light beams passing through the aperture under such a condition that the aperture area is equal to or larger than a predetermined minimum area determined from the smallest particle as a target for inspection;

a second transform optical system for forming a conjugate image of the inspected object by effecting an inverse Fourier transform on the light beams passing through the aperture; and a viewing device for viewing the conjugate image of the inspected object.

5. The apparatus according to claim 4, wherein said illuminance measuring device has:
an imaging device for imaging the Fourier transform pattern of the inspected object; and an arithmetic device for calculating the light quantity, per unit area, of the light beams passing through the aperture every time the relative positional relationship between the aperture and the Fourier transform pattern and the aperture area are changed by processing an imaging signal from said imaging device.

6. The apparatus according to claim 4, wherein said illuminance measuring device has:
a photoelectric converting device for photoelectrically converting the light beams passing through the aperture; and an arithmetic device for obtaining a light quantity, per unit area, of the light beams passing through the aperture from an aperture area set by said aperture setting device and a photoelectric conversion signal transmitted from said photoelectric converting device.

7. The apparatus according to claim 4, wherein said aperture setting device sets the aperture area to an area selected from a plurality of preset areas, and wherein said control device sets the aperture area to such an area as to minimize the light quantity, per unit area, of the light beams passing through the aperture among the plurality of preset areas.

8. A method of inspecting particles on an object, said method comprising:
a first step of obtaining a template based on a first Fourier transform pattern from a first field in the object and inspecting particles in the first field using optical data within an inspection aperture which is set in a predetermined relative positional relationship with respect to the first Fourier transform pattern; and a second step of inspecting particles in a second field different from the first field using optical data within the inspection aperture which is set in a predetermined relative positional relationship with respect to a second Fourier transform pattern from said second field;

wherein said first step involves setting a relative positional relationship between the first Fourier transform pattern and the inspection aperture to minimize a quantity of light passing through the inspection aperture; and wherein said second step involves setting said inspection aperture based on a correlation between the second Fourier transform and said template.

9. An apparatus, having a light irradiating device for irradiating an object to be inspected with beams of light for inspection and a light converging device for converging beams of light from the inspected object, for inspecting particles on the inspected object by use of the converged beams of light, said apparatus comprising:

a first transform optical system for Fourier-transforming the light beams from the inspected object;

an aperture setting device for setting an aperture having a variable relative positional relationship with the Fourier transform pattern of the inspected object and a variable area on a Fourier transform plane of the inspected object through said first transform optical system;

an illuminance measuring device for obtaining a light quantity, per unit area, of the light beams passing through the aperture;

a control device for setting the relative positional relationship between the aperture and the Fourier transform pattern and also the area of the aperture through said aperture setting device to minimize the light quantity, per unit area, of the light beams passing through the aperture under such a condition that the aperture area is equal to or larger than a predetermined minimum area determined from the smallest particle as a target for inspection; and a sensor for inspecting particles on the object using optical data within the inspection aperture.

* * * * *